(12) United States Patent
Mitamura et al.

(10) Patent No.: US 12,221,524 B2
(45) Date of Patent: Feb. 11, 2025

(54) POLYMERIZATION INITIATOR, CURABLE COMPOSITION, DENTAL MATERIAL, AND PREPARATION KIT FOR CURABLE COMPOSITION

(71) Applicant: MITSUI CHEMICALS, INC., Tokyo (JP)

(72) Inventors: Takenori Mitamura, Chiba (JP); Yoko Kosugi, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 18/336,172

(22) Filed: Jun. 16, 2023

(65) Prior Publication Data

US 2023/0323084 A1    Oct. 12, 2023

Related U.S. Application Data

(62) Division of application No. 17/057,188, filed as application No. PCT/JP2019/030517 on Aug. 2, 2019, now abandoned.

(30) Foreign Application Priority Data

Aug. 9, 2018 (JP) ................................ 2018-150314
Oct. 29, 2018 (JP) ................................ 2018-202660

(51) Int. Cl.
| C08F 4/10   | (2006.01) |
| C08F 20/10  | (2006.01) |
| C08K 5/00   | (2006.01) |
| C08K 5/092  | (2006.01) |
| C08K 5/14   | (2006.01) |
| C08K 5/3445 | (2006.01) |

(52) U.S. Cl.
CPC .............. C08K 5/3445 (2013.01); C08F 4/10 (2013.01); C08F 20/10 (2013.01); C08K 5/0025 (2013.01); C08K 5/092 (2013.01); C08K 5/14 (2013.01)

(58) Field of Classification Search
CPC .... C08K 5/3445; C08K 5/0025; C08K 5/092; C08K 5/14; C08F 4/10; C08F 20/10; A61K 6/61; A61K 6/62
See application file for complete search history.

(56) References Cited

U.S. PATENT DOCUMENTS

| 3,844,790 A     | 10/1974 | Beutel et al.      |
| 8,173,750 B2    | 5/2012  | Jakubowski et al.  |
| 8,569,421 B2    | 10/2013 | Jakubowski et al.  |
| 8,604,132 B2    | 12/2013 | Jakubowski et al.  |
| 8,815,971 B2    | 8/2014  | Jakubowski et al.  |
| 8,822,610 B2    | 9/2014  | Jakubowski et al.  |
| 9,012,528 B2    | 4/2015  | Jakubowski et al.  |
| 9,382,370 B2    | 7/2016  | Jakubowski et al.  |
| 9,399,694 B2    | 7/2016  | Jakubowski et al.  |
| 9,511,004 B2    | 12/2016 | Naruse et al.      |
| 9,518,136 B2    | 12/2016 | Jakubowski et al.  |
| 9,546,225 B2    | 1/2017  | Jakubowski et al.  |
| 9,587,064 B2    | 3/2017  | Huang et al.       |
| 9,783,628 B2    | 10/2017 | McCarthy et al.    |
| 9,856,331 B2    | 1/2018  | Jakubowski et al.  |
| 9,957,408 B2    | 5/2018  | Thompson           |
| 10,221,285 B2   | 3/2019  | Jakubowski et al.  |
| 10,259,901 B2   | 4/2019  | Huang et al.       |
| 10,654,960 B2   | 5/2020  | McCarthy et al.    |
| 10,696,798 B2   | 6/2020  | Jakubowski et al.  |
| 10,899,863 B2   | 1/2021  | Jakubowski et al.  |
| 2010/0273949 A1 | 10/2010 | Jakubowski et al.  |
| 2011/0082230 A1 | 4/2011  | Jakubowski et al.  |
| 2011/0112267 A1 | 5/2011  | Jakubowski et al.  |
| 2011/0213105 A1 | 9/2011  | Jakubowski et al.  |
| 2012/0172531 A1 | 7/2012  | Jakubowski et al.  |
| 2012/0296003 A1 | 11/2012 | Naruse et al.      |
| 2013/0296495 A1 | 11/2013 | Jakubowski et al.  |
| 2014/0024779 A1 | 1/2014  | Jakubowski et al.  |
| 2014/0024783 A1 | 1/2014  | Jakubowski et al.  |
| 2014/0155512 A1 | 6/2014  | Jakubowski et al.  |
| 2014/0357814 A1 | 12/2014 | Jakubowski et al.  |
| 2015/0191552 A1 | 7/2015  | Jakubowski et al.  |

(Continued)

FOREIGN PATENT DOCUMENTS

| JP | S4963420 A   | 6/1974 |
| JP | S58113276 A  | 7/1983 |

(Continued)

OTHER PUBLICATIONS

JPS5915469 English translation (Year: 1984).*
English translations of International Search Report and Written Opinion of the International Searching Authority issued on Sep. 17, 2019, by the Japanese Patent Office in corresponding International Patent Application No. PCT/JP2019/030517. (11 pages).

(Continued)

Primary Examiner — Catherine S Branch
Assistant Examiner — Huihong Qiao
(74) Attorney, Agent, or Firm — BUCHANAN INGERSOLL & IROONEY PC

(57) ABSTRACT

Provided is a polymerization initiator, which has an excellent curing rate and is an alternative to a polymerization initiator system using a benzoyl peroxide-aromatic amine compound, a curable composition containing the polymerization initiator, a dental material and dental filler material containing the composition, and a kit for preparing the curable composition. The polymerization initiator contains one or more compounds (A) selected from the group consisting of a pyrazolidinedione compound and/or pyrazolidine(di)thione compound (A1), a salt (A2) of the compound (A1), and a malonate compound (A3).

5 Claims, No Drawings

(56) References Cited

U.S. PATENT DOCUMENTS

| | | |
|---|---|---|
| 2015/0218438 A1 | 8/2015 | McCarthy et al. |
| 2015/0259449 A1 | 9/2015 | Jakubowski et al. |
| 2015/0376323 A1 | 12/2015 | Huang et al. |
| 2016/0040026 A1 | 2/2016 | Thompson |
| 2016/0175805 A1 | 6/2016 | Catchpole et al. |
| 2016/0184143 A1 | 6/2016 | Hooi |
| 2017/0037194 A1 | 2/2017 | Jakubowski et al. |
| 2017/0051094 A1 | 2/2017 | Jakubowski et al. |
| 2017/0135910 A1* | 5/2017 | Kudo .................... A61K 6/083 |
| 2017/0355803 A1 | 12/2017 | Huang et al. |
| 2018/0127531 A1 | 5/2018 | McCarthy et al. |
| 2018/0237551 A1 | 8/2018 | Jakubowski et al. |
| 2019/0194397 A1 | 6/2019 | Jakubowski et al. |
| 2019/0256636 A1 | 8/2019 | Huang et al. |
| 2019/0352435 A1 | 11/2019 | Jakubowski et al. |
| 2020/0277422 A1 | 9/2020 | McCarthy et al. |
| 2020/0325282 A1 | 10/2020 | Jakubowski et al. |
| 2021/0130580 A1 | 5/2021 | Mitamura et al. |

FOREIGN PATENT DOCUMENTS

| | | |
|---|---|---|
| JP | S5915469 A | 1/1984 |
| JP | 2009295895 A | 12/2009 |
| JP | 2012171955 A | 9/2012 |
| JP | 2014237856 A | 12/2014 |
| JP | 5878065 B2 | 2/2016 |
| JP | 2016094482 A | 5/2016 |
| JP | 2016520672 A | 7/2016 |
| WO | 2012157566 A1 | 11/2012 |
| WO | 2015015220 A1 | 2/2015 |
| WO | 2015015221 A1 | 2/2015 |

OTHER PUBLICATIONS

Sorenson Jr, "Copper Chelates as Possible Active Forms of the Antiarthritic", Journal of Medicinal Chemistry, 1976 (month unknown), vol. 19, Issue 1, pp. 135-148 (14 pages).

Warmkessel, et al., "Utility of malonate-initiated polymerizations of methyl methacrylate", Journal of Polymer Science: Part A: Polymer Chemistry, 1999 (month unknown), vol. 37, No. 5, pp. 615-620 (6 pages). (Cited in the Office Action issued on Mar. 25, 2022, for corresponding EP patent application No. 19846587.4).

Hino, et al., "Novel anionic thermally latent initiating systems: Anionic polymerization of glycidyl phenyl ether with potassium tert-butoxide/active methylene compounds", Journal of Polymer Science Part A: Polymer Chemistry, Jul. 25, 2004, vol. 42, No. 21, pp. 5407-5412 (6 pages). (Cited in the Office Action issued on Mar. 25, 2022, for corresponding EP patent application No. 19846587.4).

Allemann, et al., "Drug-loaded nanoparticles: preparation methods and drug targeting issues", European journal of pharmaceutics and biopharmaceutics, 1993, vol. 39, No. 5, pp. 173-191 (19 pages). (Cited in the Office Action issued on Mar. 25, 2022, for corresponding EP patent application No. 19846587.4).

* cited by examiner

POLYMERIZATION INITIATOR, CURABLE COMPOSITION, DENTAL MATERIAL, AND PREPARATION KIT FOR CURABLE COMPOSITION

CROSS-REFERENCE TO RELATED APPLICATIONS

This application is a division of U.S. patent application Ser. No. 17/057,188, filed on Nov. 20, 2020, which is a national stage of International Patent Application No. PCT/JP2019/030517, filed on Aug. 2, 2019, which claims priority to Japanese Patent Application No. 2018-150314, filed on Aug. 9, 2018, and Japanese Patent Application No. 2018-202660, filed on Oct. 29, 2018, the entire disclosures of all of which are incorporated herein by reference.

The present invention relates to a polymerization initiator, a curable composition, a dental material, and a kit for preparing a curable composition.

BACKGROUND ART

In recent years, various restorative materials have been used in dental treatment. Of these, dental curable compositions containing a radical polymerizable monomer and a radical polymerization initiator that are capable of curing the polymerizable monomers under appropriate conditions are widely used. Specific examples of the dental curable composition include dental adhesive resin cements, dental composite resins (including dental self-adhesive composite resins), dental adhesives, dental backing materials, dental root canal fillers, orthodontic adhesives, mobile tooth fixing materials, tooth fovea fissure sealant (dental sealant), dental room-temperature polymerization resins, and the like, and they are used in actual dental practice.

The main types of radical polymerization initiators contained in dental curable compositions are photopolymerization initiators, which cause polymerization and curing through irradiation with visible light, and chemical polymerization initiators, which cause polymerization and curing by mixing two or more separately stored packs immediately before use. Recently, dual cure type products containing both initiators have been also widely used in dental practice.

Among the radical polymerization initiators, the photopolymerization initiator is characterized in that polymerization inhibition by oxygen is relatively small in the course of the polymerization, and it is easy to obtain a high polymerization rate by irradiating visible light for a short time. On the other hand, since it is difficult to adapt to a part where light of an irradiator is difficult to reach, such as when a treatment part is a shaded part of a cavity or a deep part of a tooth, in that case, a dental curable composition containing a chemical polymerization initiator is mainly used.

One of common chemical polymerization initiator systems is a redox polymerization initiator, which combines an oxidizing agent and a reducing agent. A curable composition containing a redox polymerization initiator is usually divided into a first pack including an oxidizing agent and a second pack including a reducing agent and stored until immediately before use, and the first pack and the second pack are mixed at the time of use. For example, a polymerization initiator system using a first pack including benzoyl peroxide as the oxidizing agent and a second pack including an aromatic amine compound as the reducing agent is known (see, for example, Patent Literature 1).

CITATION LIST

Patent Literature

Patent Literature 1: JP 5878065 B1

SUMMARY OF INVENTION

Technical Problem

A curable composition for dental use is required to have an appropriate curing time for performing an operation. However, a polymerization initiator system using a benzoyl peroxide-aromatic amine compound described in Patent Literature 1 and the like has room for improvement in terms of curing time, and when the addition amount of benzoyl peroxide and/or aromatic amine is increased in order to improve curing rate, a cured product after curing may change from yellow to brown, or the composition may be easily cured during storage. Therefore, it is required a polymerization initiator system having an appropriate curing rate, which is an alternative to the polymerization initiator system using a benzoyl peroxide-aromatic amine compound.

The present invention has been made in view of the above circumstances, and an object thereof is to provide a polymerization initiator, which has an excellent curing rate and is an alternative to the polymerization initiator system using a benzoyl peroxide-aromatic amine compound, a curable composition containing the polymerization initiator, a dental material and dental filler material containing the composition, and a kit for preparing the curable composition.

Solution to Problem

The present inventors have found that a pyrazolidinedione compound, a pyrazolidine(di)thione compound and salts of these compounds known as anti-inflammatory agents can be used as a polymerization initiator, and a malonate compound can be used as a polymerization initiator, the compound (salt) exhibits an excellent curing rate when used in combination with a transition metal, and the cured product is suitable for a dental material, thereby completing the present invention.

The present invention includes matters described in following [1] to [12].

[1] A polymerization initiator containing one or more compounds (A) selected from the group consisting of a pyrazolidinedione compound and/or pyrazolidine(di)thione compound (A1), a salt (A2) of the compound (A1), and a malonate compound (A3).

[2] The polymerization initiator according to [1], wherein the compound (A) is one or more compounds selected from the group consisting of a pyrazolidinedione compound and/or pyrazolidine(di)thione compound (A1), and a salt (A2) of the compound (A1).

[3] The polymerization initiator according to [1] or [2], wherein the pyrazolidinedione compound and/or pyrazolidine(di)thione compound (A1) is represented by the following general formula (1).

[Chemical 1]

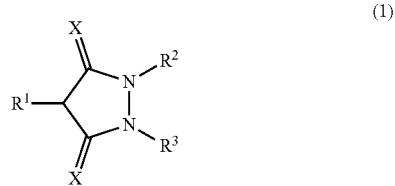

wherein $R^1$ is a hydrogen atom or a hydrocarbon group having 1 to 20 carbon atoms which may have a substituent, and the hydrocarbon group may contain a hetero atom, $R^2$ and $R^3$ are independently a hydrogen atom or a hydrocarbon group having 1 to 12 carbon atoms which may have a substituent, and the hydrocarbon group may contain a hetero atom, X represents an oxygen atom or a sulfur atom, and $R^2$ and $R^3$ may be directly bonded to each other to form a cyclic hydrocarbon group having 3 to 12 carbon atoms.

[4] The polymerization initiator according to any one of [1] to [3], which contains a transition metal compound (B).

[5] The polymerization initiator according to [4], wherein the transition metal compound (B) is a copper compound.

[6] A curable composition containing the polymerization initiator as defined in any one of [1] to [5] and a polymerizable monomer (C).

[7] The curable composition according to [6], including at least one selected from the group consisting of a peroxide (D), a filler (E), a reducing agent (F), and an aqueous solvent (G).

[8] The curable composition according to [6] or [7], which contains a photopolymerization initiator (H).

[9] A dental material containing the curable composition as defined in any one of [6] to [8].

[10] A dental filler material containing the curable composition as defined in any one of [6] to [8].

[11] A separately packed polymerization initiator including a first pack containing the compound (A) as defined in [1] and a second pack containing a transition metal compound (B).

[12] A kit for preparing a curable composition, including a first pack containing the compound (A) as defined in [1], and a second pack containing a transition metal compound (B), wherein at least one of the first pack and the second pack contains a polymerizable monomer (C).

Advantageous Effects of Invention

According to the present invention, it is possible to provide a polymerization initiator, which has an excellent curing rate and is an alternative to the polymerization initiator system using a benzoyl peroxide-aromatic amine compound, a curable composition in which a cured product of the composition is particularly suitable for a dental material by containing the polymerization initiator, and a kit for preparing a curable composition.

Description of Embodiments

The present invention will be described in detail below.
<Polymerization Initiator>

The polymerization initiator which is one embodiment of the present invention includes one or more compounds (A) selected from the group consisting of a pyrazolidinedione compound and/or pyrazolidine(di)thione compound (A1), a salt (A2) of the compound (A1), and a malonate compound (A3). These compounds (salts) are compounds having a conjugated structure in which two carbonyl groups (ketone groups) or thioxo groups (thioketone groups) are bonded to one carbon atom.

(Pyrazolidinedione Compound and/or Pyrazolidine(Di)Thione Compound (A1))

The polymerization initiator may contain a pyrazolidinedione compound and/or pyrazolidine(di)thione compound (A1) (hereinafter, also simply referred to as "compound (A1)").

The pyrazolidinedione compound of the present invention is a compound having a skeleton in which carbon atoms at positions 3 and 5 of pyrazolidine are substituted with ketone groups. Pyrazolidine(di)thione compound means a pyrazolidinethione compound or a pyrazolidinedithione compound, and the former is a compound having a pyrazolidine skeleton in which a carbon atom at position 3 of pyrazolidine is substituted with a thioketone group, and the latter is a compound having a pyrazolidine skeleton in which carbon atoms at positions 3 and 5 of pyrazolidine are substituted with thioketone groups. It is presumed that these skeletons contribute to the effect of the present invention.

The pyrazolidinedione compound and/or pyrazolidine(di)thione compound (A1) that can be contained in the polymerization initiator of the present invention is preferably a compound represented by the following general formula (1), in that excellent polymerization properties can be imparted.

[Chemical 2]

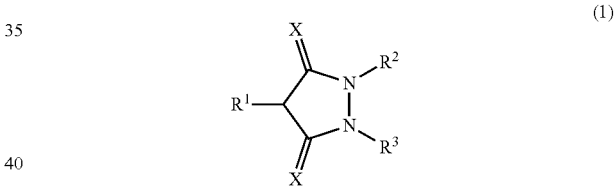

In the general formula (1), $R^1$ is a hydrogen atom or a hydrocarbon group having 1 to 20 carbon atoms which may have a substituent, and the hydrocarbon group has preferably 1 to 14 carbon atoms, and more preferably 1 to 8. The hydrocarbon group may contain a hetero atom, for example, a sulfur atom, an oxygen atom, a nitrogen atom, or the like. Further, the hydrocarbon group may be a saturated hydrocarbon group or an unsaturated hydrocarbon group. When $R^1$ is a hydrocarbon group, it may be an aromatic hydrocarbon group (aryl group (phenyl group, naphthyl group, toluyl group, benzyl group, benzoyl group), heteroaryl group (pyridyl group, etc.), aliphatic hydrocarbon group (alicyclic hydrocarbon group (cyclohexyl group, cyclopentyl group, etc.)) or a chain hydrocarbon group (alkyl group, alkenyl group, etc.), among which the chain hydrocarbon group is preferred. Among the chain hydrocarbon groups, a chain alkyl group having 1 to 14 carbon atoms is preferable, a chain alkyl group having 2 to 12 carbon atoms is more preferable, and a chain alkyl group having 3 to 8 carbon atoms is particularly preferable.

$R^2$ and $R^3$ are independently a hydrogen atom or a hydrocarbon group having 1 to 12 carbon atoms which may have a substituent. In the case of a hydrocarbon group, they may be an aromatic hydrocarbon group (aryl group (phenyl group, naphthyl group, toluyl group, benzyl group, benzoyl group, etc.), a heteroaryl group (pyridyl group, etc.)), an aliphatic hydrocarbon group (alicyclic hydrocarbon group (cyclohexyl group, cyclopentyl group, etc.) or a chain hydrocarbon group (alkyl group, alkenyl group, etc.), and the aromatic hydrocarbon group is more preferred. Among the aromatic hydrocarbon groups, the phenyl group is particularly preferable. Moreover, $R^2$ and $R^3$ may be directly bonded to each other to form a cyclic hydrocarbon group having 3 to 12 carbon atoms. Further, the hydrocarbon group may contain a hetero atom, for example, a sulfur atom, an oxygen atom, a nitrogen atom, or the like. Furthermore, the hydrocarbon group may be a saturated hydrocarbon group or an unsaturated hydrocarbon group.

X is an oxygen atom or a sulfur atom, and preferably an oxygen atom.

When $R^2$, $R^2$ and $R^3$ are hydrocarbon groups, examples of a substituent that $R^2$, $R^2$ and $R^3$ may have include a halogen atom, a hydroxyl group, a carboxy group, an alkoxy group, an oxo group, an amino group, an amide group, a nitro group, a cyano group, a sulfide group, a sulfinyl group, a sulfoxy group, and the like.

Molecular weight of the pyrazolidinedione compound and/or pyrazolidine(di)thione compound (A1) that can be contained in the polymerization initiator of the present invention may be, for example, 100 to 800, and is preferably 150 to 600, and more preferably 200 to 500.

Examples of the pyrazolidinedione compound include 1,2-diphenyl-3,5-pyrazolidinedione, 4-butyl-1,2-diphenyl-3,5-pyrazolidinedione (phenylbutazone), 1,2-diphenyl-4-propyl-3,5-pyrazolidinedione, 4-(1-methylethyl)-1,2-diphenyl-3,5-pyrazolidinedione, 1,2-diethyl-3,5-pyrazolidinedione, 1,2-dimethyl-4-(3-oxobutyl)-1,2-diphenyl-3,5-pyrazolidinedione (ketophenylbutazone), 4-(2-oxopropyl)-1,2-diphenyl-3,5-pyrazolidinedione, 4-butyl-1,2-dimethyl-3,5-pyrazolidinedione, 4-(3-hydroxybutyl)-1,2-diphenyl-3,5-pyrazolidinedione (α-hydroxyphenylbutazone), 4-butyl-1-(4-hydroxyphenyl)-2-phenyl-3,5-pyrazolidinedione (oxyphenbutazone), 1-(4-(benzyloxy)phenyl)-4-butyl-2-phenyl-3,5-pyrazolidinedione (4'-O-benzyloxyphenbutazone), 1,2-diphenyl-4-[2-(phenylsulfinyl)ethyl]-3,5-pyrazolidinedione (sulfinpyrazone), 4-(2-aminoethyl)-1,2-diphenyl-3,5-pyrazolidinedione, 4-(3-methyl-2-butenyl)-1,2-diphenyl-3,5-pyrazolidinedione (feprazone), 4-(4,4-dimethyl-3-oxophenyl)-1,2-diphenyl-3,5-pyrazolidinedione (tribuzone), 4,4'-(4-butyl-3,5-dioxopyrazolidine-1,2-diyl) dibenzenesulfonamide (butacuglionamide), 4-[2-(methylthio)ethyl]-1,2-diphenyl-3,5-pyrazolidinedione, 1,2-dimethyl-3,5-pyrazolidine-4-carbonitrile, 2-[(2-tetrahydrofuranyl)methyl]-1H-benzo[c]pyrazolo[1,2-a]cinnoline-1,3(2H)-dione (cinnofuradione) and 1,1',2,2'-tetraphenyl-(4,4'-bipyrazolidine)-3,3',5,5'-tetrone and the like; and examples of the pyrazolidine(di)thione compound include 1,2-diphenyl-3,5-pyrazolidinedione, 4-butyl-1,2-diphenyl-3,5-pyrazolidinedithione, and the like.

Of these, phenylbutazone and 4-butyl-1,2-diphenyl-3,5-pyrazolidinedithione are preferable, and phenylbutazone is particularly preferable.

The compound (A1) can be produced by a known method. For example, in the case of phenylbutazone, it can be obtained by heating and refluxing hydrazobenzene and diethyl butylmalonate in the presence of sodium sulfite using methanol as a solvent, and oxidizing the obtained phenylbutazone salt with acetic acid.

In addition, a commercially available product can be purchased as the compound (A1). As the commercially available product, for example, phenylbutazone can be purchased from Tokyo Chemical Industry Co., Ltd., FUJIFILM Wako Pure Chemical Corporation, and the like. The compound (A1) may be used alone or in combination of two kinds.

(Salt (A2) of Compound (A1))

The polymerization initiator may contain a salt (A2) of the compound (A1) (i.e., a salt of a pyrazolidinedione compound and/or a salt of a pyrazolidine(di)thione compound) (hereinafter, also simply referred to as "salt (A2)").

The salt (A2), like the compound (A1), is excellent in that it can give a curing rate and excellent mechanical strength. In addition, the salt (A2) is excellent in usability because it does not easily cure during storage when it is added to the curable composition in a large amount.

The type of salt of the salt (A2) is not particularly limited, but a metal salt is preferable. The metal is not particularly limited, but is preferably one or more metals selected from the group consisting of alkali metals, alkaline earth metals and transition metals, and more preferably one or more metals selected from the group consisting of alkali metals and alkaline earth metals.

Examples of the alkali metal include lithium, sodium, potassium, and the like.

Examples of the alkaline earth metal include magnesium, calcium, strontium, and the like.

Examples of the transition metal salt include copper, vanadium, titanium, manganese, iron, cobalt, nickel, and the like.

Of these, the salt (A2) is preferably one or more metals selected from the group consisting of calcium and sodium.

The salt (A2) is preferably a salt of the compound represented by the general formula (1), while maintaining sufficient polymerization properties, in that excellent operability can be imparted, and more preferably a salt represented by the following general formula (2).

[Chemical 3]

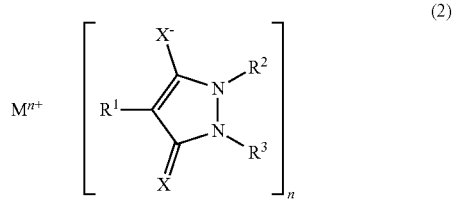

In the general formula (2), $R^2$, $R^2$, $R^3$ and X have the same meaning as in the general formula (1). Further, in the general formula (2), preferred embodiments and specific examples of $R^2$, $R^2$, $R^3$ and X are the same as those in the general formula (1). Furthermore, in the general formula (2), $M^{n+}$ represents an n-valent metal cation, and n represents an integer of 1 to 5.

The metal M in $M^{n+}$ is the same as a metal in a metal salt of the salt (A2). That is, the metal is preferably one or more metals of alkali metals, alkaline earth metals and transition metals, more preferably one or more metals selected from the group consisting of alkali metals and alkaline earth metals, and further preferably one or more metals selected from the group consisting of calcium ion and sodium ion.

The compound (A1) constituting the salt (A2) may have a molecular weight of, for example, 100 to 800, and is preferably 150 to 600, and more preferably 200 to 500.

Examples of the salt of the pyrazolidinedione compound and the salt of the pyrazolidine(di)thione compound include salts of pyrazolidinedione compounds such as phenylbutazone, and pyrazolidine(di)thione compounds such as 4-butyl-1,2-diphenyl-3,5-pyrazolidinedithione, exemplified as the pyrazolidinedione compound and/or the pyrazolidine (di)thione compound in the section of (Pyrazolidinedione compound and/or pyrazolidine(di)thione compound (A1)).

Of these, salts of phenylbutazone and 4-butyl-1,2-diphenyl-3,5-pyrazolidinedithione are preferable, and salts of phenylbutazone are particularly preferable.

The salt (A2) can be produced by a known method. For example, in the case of the salt of phenylbutazone, the salt of phenylbutazone can be obtained by heating and refluxing hydrazobenzene and diethyl butylmalonate in the presence of sodium sulfite using methanol as a solvent.

In addition, a commercially available product can be purchased as the salt (A2). As the commercially available product, for example, phenylbutazone calcium and phenylbutazone sodium can be purchased from Woongjin Chemical Co., Ltd., and the like. The salts (A2) may be used alone or in combination of two kinds.

(Malonate Compound (A3))

The polymerization initiator may contain a malonate compound (A3) (hereinafter, also simply referred to as "compound (A3)"). The malonate compound (A3) is a compound having an ester bond in at least one carboxy group of malonic acid, and is preferably a malonate compound represented by the following general formula (3).

[Chemical 4]

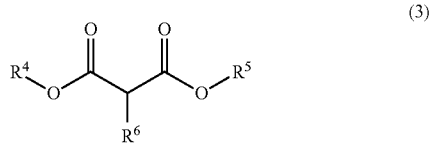

(3)

wherein $R^4$ and $R^5$ are each independently a hydrocarbon group having 1 to 12 carbon atoms which may have a substituent, and the hydrocarbon group may contain a hetero atom, $R^6$ is a hydrocarbon group having 1 to 20 carbon atoms which may have a substituent, and the hydrocarbon group may contain a hetero atom.

Examples of the compound (A3) include diethyl phenylmalonate (DEPM), triethyl methanetricarboxylate (TEMTC), diethyl methylmalonate, diethyl ethylmalonate, diethyl allylmalonate, dimethyl methoxymalonate, dimethyl benzylmalonate, dimethyl cyclopentylmalonate, diethyl benzoylmalonate, diethyl 2-(2-cyanoethyl)malonate, diethyl phthalimidomalonate, diethyl 2-acetylmalonate, and the like. Of these, diethyl phenylmalonate and triethyl methanetricarboxylate are preferable, and diethyl phenylmalonate is more preferable.

The compound (A3) can be produced by a known method. For example, in the case of diethyl phenylmalonate, ethyl oxalate is reacted with ethyl phenylacetate in an ethanol solution in which sodium is dissolved, and phenyloxaloacetate is released from the obtained sodium salt with sulfuric acid, it can be synthesized by heating under reduced pressure to remove carbon monoxide produced.

Further, for example, in the case of triethyl methanetricarboxylate, it can be synthesized by reacting anhydrous alcohol, magnesium carbon tetrachloride and diethyl malonate, reacting the obtained diethyl ethoxymagnesiomalonate with ethyl chloroformate in the presence of diethyl ether, and decomposing the obtained reaction product with dilute acetic acid.

In addition, a commercially available product can be purchased as the compound (A3). As the commercially available product, for example, diethyl phenylmalonate and triethyl methanetricarboxylate can be purchased from FUJIFILM Wako Pure Chemical Corporation, Tokyo Chemical Industry Co., Ltd., Kanto Chemical Co., Inc., and the like. The compound (A3) may be used alone or in combination of two kinds.

The compound (A1), salt (A2) and compound (A3) may be used in any combination. That is, they may be used in combinations of compound (A1) and salt (A2), salt (A2) and compound (A3), compound (A1) and compound (A3), and compound (A1), salt (A2) and compound (A3).

(Transition Metal Compound (B))

The polymerization initiator of the present invention preferably contains a transition metal compound (B). Polymerization starts by using the compound (A) and a transition metal compound (B) together in the presence of a polymerizable monomer (C) described later. In addition, it is preferable that the transition metal compound (B) is stored as a separately packed polymerization initiator described later so that the transition metal compound (B) does not contact and react with the compound (A) during storage. Moreover, the transition metal compound (B) does not include a transition metal salt of the salt (A2).

Examples of the transition metal compound (B) include copper compounds, molybdenum compounds, vanadium compounds, scandium compounds, titanium compounds, chromium compounds, manganese compounds, iron compounds, cobalt compounds, nickel compounds, and the like.

Examples of the copper compound include monovalent or divalent copper compounds such as copper acetylacetonate, copper oleate, copper acetate, copper gluconate, copper citrate, copper phthalate, copper naphthenate, copper hydroxide, copper methoxide, copper ethoxide, copper isopropoxide, copper chloride, and copper bromide.

The vanadium compound is preferably at least one compound selected from trivalent to pentavalent vanadium compounds, and examples thereof include vanadium(III) acetylacetonate, vanadium(III) naphthenate, vanadyl stearate, vanadium benzoylacetonate, bis(maltolate) oxovanadium (IV), oxobis(1-phenyl-1,3-butanedionate) vanadium(IV), and vanadyl(IV) acetylacetonate.

Examples of the molybdenum compound include molybdenum(IV) oxide, molybdenum oxide acetylacetonate, molybdenium ethoxide, bis(2,4-pentadionato)molybdenium oxide, molybdenyl diethyldithiocarbamate, and the like.

Examples of the iron compound include divalent or trivalent iron compounds such as iron acetylacetonate, ferrocene, iron acetate, iron stearate, iron 2-ethylhexanoate, iron oxalate, iron citrate, iron gluconate, iron nitrate, iron sulfate, iron phosphate, iron perchlorate, iron oxide, iron sulfide, iron fluoride, iron chloride, iron bromide, potassium hexacyanoferrate, and iron ethoxide.

Examples of the cobalt compound include divalent or trivalent cobalt compounds such as cobalt acetylacetonate, cobalt acetate, cobalt naphthenate, cobalt oleate, cobalt stearate, cobalt 2-ethylhexanoate, cobalt benzoate, cobalt oxalate, cobalt citrate, cobalt carbonate, cobalt nitrate, cobalt sulfate, cobalt phosphate, cobalt perchlorate, cobalt thiocyanate, cobalt oxide, cobalt sulfide, cobalt fluoride, cobalt chloride, cobalt bromide, cobalt hydroxide, and cobalt isopropoxide.

Examples of the nickel compound include divalent nickel compounds such as nickel acetylacetonate, bis(dithiobenzil) nickel, bis(cyclopentadienyl)nickel, nickel formate, nickel acetate, nickel lactate, nickel naphthenate, nickel 2-ethylhexanoate, nickel oxalate, nickel citrate, nickel stearate, nickel perchlorate, nickel oxide, nickel sulfide, nickel fluoride, nickel chloride, nickel bromide, nickel iodide, nickel carbonate, nickel nitrate, nickel sulfate, nickel hydroxide, and nickel ethoxide.

Examples of the scandium compound include scandium (III) iodide and the like. Examples of the titanium compound include titanium(IV) chloride, titanium(IV) tetraisopropoxide, and the like. Examples of the chromium compound include chromium(II) chloride, chromium(III) chloride, chromic acid, chromate, and the like. Examples of the manganese compound include manganese(II) chloride, manganese(II) acetate, manganese(II) oxide, manganese(III) oxide, manganese(II) nitrate, and the like.

Among these transition metals, a copper compound is preferable because it has high polymerization properties to be imparted to the composition.

The transition metal compound (B) may be used singly or in combination of two or more thereof. Further, the content of the transition metal compound (B) in the polymerization initiator of the present invention is preferably 0.0001 to 200 parts by mass, more preferably 0.0005 to 150 parts by mass, and particularly preferably 0.001 to 100 parts by mass, based on 100 parts by mass of the compound (A).

<Separately Packed Polymerization Initiator>

Another embodiment of the present invention is a separately packed polymerization initiator including a first pack containing the compound (A) and a second pack containing the transition metal compound (B).

By storing the compound (A) and the transition metal compound (B) in separate containers or the like, it can be stored without reacting the compound (A) with the transition metal compound (B) during storage.

The content of the transition metal compound (B) in the second pack is preferably 0.0001 to 200 parts by mass, more preferably 0.0005 to 150 parts by mass, and particularly preferably 0.001 to 100 parts by mass, based on 100 parts by mass of the compound (A) in the first pack.

<Curable Composition>
(Polymerizable Monomer (C))

The curable composition according to another embodiment of the present invention contains the polymerization initiator and a polymerizable monomer (C). Herein, "(meth) acryl" means acryl or methacryl, and for example, "(meth) acrylic acid" means acrylic acid or methacrylic acid. Similarly, "(meth)acryloyl" means "acryloyl" or "methacryloyl", and "(meth)acrylate" means "acrylate" or "methacrylate".

The polymerizable monomer (C) is not particularly limited as long as polymerization can be initiated by the polymerization initiator of the present invention, and examples thereof include a radical polymerizable monomer. Further, the radical polymerizable monomer preferably has, as a radical polymerizable unsaturated group, a (meth) acryloyl group, a (meth)acrylamide group, a styryl group, a vinyl group, an allyl group or the like, more preferably has a (meth)acryloyl group or a (meth)acrylamide group, and further preferably has a methacryloyl group.

Examples of the radical polymerizable monomer include hydroxyalkyl (meth)acrylates such as 2-hydroxyethyl (meth)acrylate, 3-hydroxypropyl (meth)acrylate, 4-hydroxybutyl (meth)acrylate, 6-hydroxyhexyl (meth)acrylate, and 10-hydroxydecyl (meth)acrylate; monofunctional monomers such as 2-(dimethylamino)ethyl methacrylate, N-methyl-N-phenylaminoethyl (meth)acrylate, N-ethyl-N-phenylaminoethyl (meth)acrylate, propyleneglycol mono (meth)acrylate, glycerol mono(meth)acrylate, erythritol mono(meth)acrylate, and N-hydroxyethyl(meth)acrylamide; bifunctional monomers having an aromatic ring such as 2,2-bis((meth)acryloyloxyphenyl)propane, 2,2-bis[4-(3-(meth)acryloyloxy-2-hydroxypropoxy)phenyl]propane (commonly known as "Bis-GMA"); bifunctional monomer having an aliphatic carbon chain such as glycerol di(meth) acrylate, triethyleneglycol di(meth)acrylate, neopentylglycol di(meth)acrylate, 1,6-hexanediol di(meth)acrylate, 2,2, 4-trimethylhexamethylene bis(2-carbamoyloxyethyl) dimethacrylate (commonly known as "UDMA"), 1,2-bis(3-(meth)acryloyloxy-2-hydroxypropoxy)ethane, and 1,6-hexanediol dimethacrylate (HexDMA); trifunctional or more polyfunctional monomers such as trimethylolpropane tri(meth)acrylate, tris(2-(meth)acryloxyethyl)isocyanurate, and dipentaerythritol penta(meth)acrylate; polymerizable monomers synthesized by addition reaction of a compound having an isocyanate group (—NCO) such as hexamethylene diisocyanate (HDI), tolylene diisocyanate (TDI), xylylene diisocyanate (XDI), diphenylmethane diisocyanate (MDI), isophorone diisocyanate (IPDI), trimethylhexamethylene diisocyanate (TMHMDI) or norbornane diisocyanate (NBDI) with a (meth)acrylate group having a hydroxyl group (—OH) such as 2-hydroxyethyl (meth)acrylate or 2-hydroxypropyl (meth)acrylate (for example, described in WO 2012/157566 A, WO 2015/015220 A, WO 2015/015221 A, and JP 2016-094482 A); acid group-containing polymerizable monomers containing a carboxylic acid group (4-methacryloyloxyethyl trimellitic acid (4-MET), etc.), a carboxylic acid anhydride group, a phosphoric acid group (10-methacryloyloxydecyl dihydrogen phosphate (MDP), etc.), a thiophosphoric acid, a pyrophosphate group, a thiopyrophosphate group, a phosphoric acid group, a thiophosphonic acid group, a sulfonic acid group and the like in the same compound, and those in which these acidic groups are in the form of an acid chloride, an alkali metal salt, an alkaline earth metal salt, an ammonium salt, and the like; organosilicon compounds having a polymerizable group such as γ-methacryloxyalkyltrimethoxysilane (γ-MPTS); and the like.

Among these, from the viewpoint of physical properties and ease of handling, 2,2,4-trimethylhexamethylene bis(2-carbamoyloxyethyl) dimethacrylate (UDMA), bisphenol A diglycidyl methacrylate (Bis-GMA), 2-hydroxyethyl methacrylate (HEMA), triethylene glycol dimethacrylate (TEGDMA), 1,6-hexanediol dimethacrylate (HexDMA), NBDI-HEA (synthetic compound of norbornane diisocyanate and 2-hydroxyethyl acrylate), 10-methacryloyloxydecyl dihydrogen phosphate (MDP) and 4-methacryloyloxyethyl trimellitic acid (4-MET) are preferred.

The polymerizable monomer (C) may be used singly or in combination of two or more thereof. Further, the content of the polymerizable monomer (C) in the curable composition of the present invention is preferably 100 to 100,000 parts by mass, more preferably 500 to 50,000 parts by mass, and particularly preferably 1,000 to 20,000 parts by mass, based on 100 parts by mass of the polymerization initiator 100 parts by mass of pyrazolidinedione salt compound and/or pyrazolidine(di)thione salt compound (A2).

The curable composition of the present invention preferably contains at least one selected from the group consisting of a peroxide (D), a filler (E), a reducing agent (F), and an aqueous solvent (G). Further, the curable composition of the present invention may contain a photopolymerization initiator (H).

(Peroxide (D))

A peroxide (D) is preferably contained in the curable composition of the present invention, in that polymerization properties of the composition are improved and the obtained cured product tends to have excellent mechanical strength and adhesive strength. Examples of the peroxide (D) include peroxy ester compounds, hydroperoxide compounds, alkyl peroxides, and the like. Of these, the peroxyester compound is preferable from the viewpoint of storage stability and reactivity.

As the peroxyester compound, any known one can be used without any limitation as long as it has an acyl group on one side of a peroxy group (—OO—) and a hydrocarbon group on the other side (or an organic group similar thereto). Examples of the peroxyester compound include t-butyl peroxyneodecanoate, t-butyl peroxyisobutyrate, t-butyl peroxymaleic acid, t-butyl peroxyisopropyl monocarbonate, t-butyl peroxyester isononanoate, t-butyl peroxyacetate, t-butyl peroxybenzoate (tBPB), t-butyl peroxy-m-toluoylbenzoate, cumyl peroxyneodecanoate, 1,1,3,3-tetramethylbutyl peroxyneodecanoate, 1-cyclohexyl-1-methylethyl peroxyneodecanoate, t-hexyl peroxyneodecanoate, 2,5-bis(benzoylperoxy)hexane, t-amyl peroxyisononanoate (tAPiN), and the like.

As the peroxyester compound, any known one can be used without any limitation as long as it has a hydrocarbon group (or an organic group similar thereto) on one side of a peroxy group (—OO— group), and hydrogen on the other side. Specific examples thereof include p-menthane hydroperoxide, diisopropylbenzene hydroperoxide, 1,1,3,3-tetramethylbutyl hydroperoxide (TMBHP), cumene hydroperoxide, t-hexyl hydroperoxide, and t-amyl hydroperoxide.

As the alkyl peroxide, any known one can be used without any limitation as long as it has a hydrocarbon group (or an organic group similar thereto) in both sides of a peroxy group (—OO— group). Examples of the alkyl peroxide include di-t-butyl peroxide, di-t-hexyl peroxide, 1,1-bis(t-butylperoxy)cyclohexane (tBPCy), and the like.

Among these peroxides (D), from the viewpoint of storage stability and reactivity, t-butyl peroxybenzoate (tBPB), t-butyl peroxyester isononanoate, t-amyl peroxyisononanoate (tAPiN), 1,1,3,3-tetramethylbutyl hydroperoxide (TMBHP), cumene hydroperoxide and 1,1-di(t-butylperoxy)cyclohexane (tBPCy) are preferable, t-butyl peroxybenzoate (tBPB), t-amyl peroxyisononanoate (tAPiN), 1,1,3,3-tetramethylbutyl hydroperoxide (TMBHP), cumene hydroperoxide are more preferable, and t-butyl peroxybenzoate (tBPB) and t-amyl peroxyisononanoate (tAPiN) are particularly preferred.

The peroxide (D) may be used singly or in combination of two or more thereof. Further, the content of the peroxide (D) in the curable composition of the present invention is preferably 1 to 1000 parts by mass, more preferably 10 to 700 parts by mass, and particularly preferably 50 to 500 parts by mass, based on 100 parts by mass of the polymerization initiator.

(Filler (E))

A filler (E) is preferably contained in the curable composition of the present invention, in that fluidity and consistency, color tone, curability and the like of the composition are adjusted, radiodensity is imparted, and mechanical strength of the obtained cured product is improved. As the filler (E), a general filler used in the dental field can be used. Fillers are generally broadly classified into organic fillers and inorganic fillers.

Examples of the organic filler include powdered polymer fillers obtained by pulverization of a polymer or dispersion polymerization, and fillers obtained by polymerizing a polymerizable monomer with a crosslinking agent and then pulverizing the resulting polymer. Specific examples of such an organic filler include fine powders of a homopolymer or copolymer of a polymerizable monomer, such as polymethyl methacrylate (PMMA), polybutyl methacrylate (PBMA), polyvinyl acetate (PVAc), polyethylene glycol (PVA), polyurethane, polyurea, methyl methacrylate-ethyl methacrylate copolymer, crosslinked polymethyl methacrylate, ethylene-vinyl acetate copolymer, and styrene-butadiene copolymer. Further, the organic filler may also be a product obtained by adding a component such as a known pigment, a fluorescent agent, a biologically active component, a polymerization initiator, and the like during preparation of the organic filler.

Examples of the inorganic filler include fine powders of various glasses (mainly composed of silicon dioxide, containing oxides such as heavy metals, boron and aluminum as necessary), various ceramics, diatomaceous earth, kaolin, clay mineral (montmorillonite, etc.), activated clay, synthetic zeolite, mica, calcium fluoride, ytterbium fluoride, calcium carbonate, calcium phosphate, aluminum sulfate, barium sulfate, calcium sulfate, zirconium dioxide, titanium dioxide, aluminum oxide, boron oxide, barium oxide, lanthanum oxide, strontium oxide, zinc oxide, calcium oxide, lithium oxide, sodium oxide, bismuth oxide, yttrium oxide, calcium phosphate, hydroxyapatite, aluminum hydroxide, sodium fluoride, potassium fluoride, sodium monofluorophosphate, lithium fluoride, and the like. Specific examples of such inorganic fillers include, for example, fine powders of barium borosilicate glasses (such as Kimble RAY-SORB T3000, Schott 8235, Schott GM27884, and Schott G018-053), fine powders of strontium boroaluminosilicate glasses (such as RAY-SORB T4000, Schott G018-093 and G018-163), fine powders of lanthanum glass (such as Schott GM31684 and G018-161), fine powders of fluoroaluminosilicate glasses (such as Schott G018-091 and Schott G018-117), and fine powders of boroaluminosilicate glasses containing zirconium and/or cesium (such as Schott G018-307, G018-308 and G018-310).

It is also possible to use an organic-inorganic composite filler obtained by: adding a polymerizable monomer to the above-mentioned inorganic fillers in advance to form a paste, then polymerizing and curing, and pulverizing the resultant product. Examples of the organic-inorganic composite filler include a filler (TMPT·f) obtained by polymerizing and coating fine powder silica, zirconium oxide or the like of an inorganic filler with a polymerizable monomer having trimethylolpropane tri(meth)acrylate (TMPT) as a main component, and then pulverizing the obtained polymer, and the like.

When a microfiller with a particle size of 0.1 μm or less is incorporated in a dental material, it is advantageous in obtaining polishing smoothness and abrasion resistance of the cured product, and it is one preferred mode of the dental composite resin. As a material of the filler with such a particle size, silica (trade name: Aerosil R812, R972, etc.), alumina, zirconia, titania and the like are preferable.

These fillers (E) are subjected to surface treatment with a silane coupling agent or the like according to the purpose. For example, when using an inorganic filler or an organic-inorganic composite filler, it is preferred to treat a filler surface with a known surface treating agent to improve affinity and dispersibility with the polymerizable monomer (C) used in the present invention. As such a surface treatment agent, a known silane coupling agent can be used without any limitation. For example, γ-methacryloxyalkyltrimethoxysilane (number of carbons between methacryloxy group and silicon atom: 3 to 12), γ-methacryloxyalkyltriethoxysilane (number of carbons between methacryloxy group and silicon atom: 3 to 12), or an organosilicon compound such as vinyltrimethoxysilane, vinylethoxysilane, and vinyltriacetoxysilane can be used. In addition to the silane coupling agent, a surface treatment may be performed with a titanate coupling agent, an aluminate coupling agent, a zirco-aluminate coupling agent, or the like.

These fillers (E) can be appropriately added according to the application. The filler (E) may be used singly or in combination of two or more thereof. Moreover, when the filler (E) is added, the content is preferably 1 to 900 parts by mass, more preferably 10 to 600 parts by mass, and particularly preferably 60 to 500 parts by mass, based on 100 parts by mass of the polymerizable monomer (C) contained in the composition of the present invention.

(Reducing Agent (F))

A reducing agent (F) is preferably contained in the curable composition of the present invention, in terms of polymerization efficiency. As the reducing agent (F), any known one can be used without any limitation. As the reducing agent (F), an amine compound or a salt thereof, a sulfinic acid compound or a salt thereof, an ascorbic acid compound or a salt thereof can be used, and a sulfinic acid compound or a salt thereof is preferable.

Examples of the amine compound include aromatic-substituted glycine compounds or salts thereof, and aromatic tertiary amines. Examples of the aromatic-substituted glycine compound or salt thereof include aromatic-substituted glycine, or usual alkali metal salts, alkaline earth metal salts, amine salts, and ammonium salts thereof. Examples of the alkali metal salt include lithium salts, sodium salts, potassium salts, and the like. Examples of the alkaline earth metal salt include magnesium salts, calcium salts, strontium salts, and barium salts. Examples of the amine salt include salts of primary amines such as methylamine; secondary amine salts such as dimethylamine; salts of tertiary amines such as trimethylamine. Examples of the salt of the ammonium compound include ammonium salts, tetramethylammonium salts, tetraethylammonium salts, tetrapropylammonium salts, and trimethylbenzylammonium salts.

Examples of the aromatic tertiary amine include N,N-dimethylaniline (DMA), N,N-dimethyl p-toluidine (DMPT), N,N-diethyl p-toluidine, N,N-diethanol p-toluidine (DEPT); methyl N,N-dimethylaminobenzoate, ethyl N,N-dimethylaminobenzoate (DMABAE), butoxyethyl N,N-dimethylaminobenzoate (DMABABE), N,N-diethylaminobenzoic acid (DEABA) and alkyl esters thereof, N,N-dimethylaminobenzaldehyde (DMABAd), N,N-dimethylaminobenzophenone, and the like.

As the sulfinic acid compound or salt thereof, a sulfinic acid or a usual alkali metal salt, alkaline earth metal salt, amine salt or ammonium salt of a sulfinic acid can be used. Examples of the alkali metal salt include lithium salts, sodium salts, potassium salts, and the like. Examples of the alkaline earth metal salt include magnesium salts, calcium salts, strontium salts, barium salts, and the like. Examples of the amine salt include salts of primary amines such as methylamine; secondary amine salts such as dimethylamine; salts of tertiary amines such as trimethylamine. Examples of the salt of the ammonium compound include ammonium salts, tetramethylammonium salts, tetraethylammonium salts, tetrapropylammonium salts, and trimethylbenzylammonium salts.

Further, as the sulfinic acid compound or salt thereof, an organic sulfinic acid or a salt thereof can be used. Examples of the organic sulfinic acid compound include alkanesulfinic acids such as methanesulfinic acid; alicyclic sulfinic acids such as cyclohexanesulfinic acid and cyclooctanesulfinic acid; and aromatic sulfinic acids such as benzenesulfinic acid, p-toluenesulfinic acid decylbenzenesulfinic acid chlorobenzenesulfinic acid, fluorobenzenesulfinic acid, and naphthalenesulfinic acid.

Examples of the salt of an organic sulfinic acid compound include salts of alkali metals such as lithium, sodium and potassium, salts of alkaline earth metals such as magnesium, calcium and strontium, amine salts such as triethylamine, and ammonium salts such as tetrabutylammonium of the above organic sulfinic acid compounds, and the like. Examples thereof include sodium p-toluenesulfinate (p-TSS), potassium p-toluenesulfinate, calcium p-toluenesulfinate, and the like.

Among the sulfinic acid compounds or salts thereof, sodium p-toluenesulfinate (p-TSS) is preferable in terms of reactivity and easy handling.

When the reducing agent (F) is added, the content is preferably 0.00001 to 20 parts by mass, more preferably 0.00005 to 10 parts by mass, and particularly preferably 0.0001 to 5 parts by mass, based on 100 parts by mass of the polymerizable monomer (C) contained in the composition of the present invention.

(Aqueous Solvent (G))

The curable composition of the present invention can also contain an aqueous solvent (G). As the aqueous solvent (G), any known one can be used without any limitation, and water, physiological saline, an organic solvent miscible with water, or a mixed solvent thereof can be used. Examples of water that can be used include distilled water and ion-exchanged water. Examples of the organic solvent miscible with water include alcohols such as methanol, ethanol and isopropanol, ketones such as acetone and methyl ethyl ketone, ethers such as tetrahydrofuran, amides such as N,N-dimethylformamide, and aprotic solvents such as dimethyl sulfoxide. Among these organic solvents, it is preferable to use ethanol or acetone in consideration of harmfulness and irritation to dental pulp.

These aqueous solvents (G) can be appropriately added according to the application. When the aqueous solvent (G) is added, the content is preferably 10 to 900 parts by mass, more preferably 25 to 500 parts by mass, and particularly preferably 100 to 300 parts by mass, based on 100 parts by mass of the polymerizable monomer (C) contained in the composition of the present invention.

(Photopolymerization Initiator (H))

The curable composition of the present invention can also contain a photopolymerization initiator (H). As the photopolymerization initiator (F), any known one can be used without any limitation. As the photopolymerization initiator, for example, α-diketone/reducing agent, ketal/reducing agent, thioxanthone/reducing agent, an acylphosphine oxide compound and the like can be used.

Examples of the α-diketone include camphorquinone (CQ), camphorquinonesulfonic acid, camphorquinonecarboxylic acid, 1,2-cyclohexanedione, methylglyoxal, phenylglyoxal, pyruvic acid, benzoylformic acid, phenylpyruvic acid, methyl pyruvate, ethyl benzoylformate, methyl phenylpyruvate, and the like.

Examples of the ketal include benzyl dimethyl ketal, benzyl diethyl ketal, and the like.

Examples of the thioxanthone include 2-chlorothioxanthone, 2,4-diethylthioxanthone, and the like.

Examples of the acylphosphine oxide compound include 2,4,6-trimethylbenzoyldiphenylphosphine oxide (TPO), bis (2,6-dimethoxybenzoyl)-2,4,4-trimethylpentylphosphine oxide, bis(2,4,6-trimethylbenzoyl)-phenylphosphine oxide, and the like.

Examples of the reducing agent include hydrogen peroxide, Michler's ketone; aldehydes such as citronellal, lauryl aldehyde, phthaldialdehyde, dimethylaminobenzaldehyde and terephthalaldehyde; mercaptans such as 2-mercaptobenzoxazal, decanethiol, 3-mercaptopropyltrimethoxysilane, 4-mercaptoacetophenone, thiosalicylic acid, and thiobenzoic acid;

aromatic amine compounds such as N,N-dimethylaminobenzoic acid and alkyl esters thereof, such as N,N-dimethylaminobenzoic acid ethyl (DMABAE) and N,N-dimethylaminobenzoic acid butoxyethyl (DMABABE), N,N-diethylaminobenzoic acid (DEABA) and alkyl esters thereof, N,N-dimethylaminobenzaldehyde (DMABAd), N,N-dimethylaminobenzophenone, N,N-dimethylaniline (DMA), N,N-dimethyl-p-toluidine (DMPT), and N,N-di(2-hydroxyethyl)-p-toluidine (DEPT); and the like.

Among the above photopolymerization initiators (H), in view of having an absorption wavelength in the visible light region and being polymerizable by visible light, a photopolymerization initiator containing camphorquinone or TPO having an absorption wavelength at 400 nm or more is preferred, and in particular, a photopolymerization initiator containing camphorquinone having an absorption wavelength at 468 nm is preferred, and a photopolymerization initiator containing camphorquinone and ethyl N,N-dimethylaminobenzoate is more preferred.

Examples of the photopolymerization initiator containing camphorquinone/reducing agent includes a photopolymerization initiator containing camphorquinone/aromatic amine compound, a photopolymerization initiator containing camphorquinone/peroxide, a photopolymerization initiator camphorquinone/aldehyde, and a photopolymerization initiator containing camphorquinone/mercaptan.

The photopolymerization initiator (H) may be used singly or in combination of two or more thereof. Further, the content of the photopolymerization initiator (H) is preferably 0.001 to 5 parts by mass, more preferably 0.005 to 3 parts by mass, and particularly preferably 0.01 to 1 part by mass, based on 100 parts by mass of the polymerizable monomer (C) contained in the composition of the present invention.

(Other Ingredients)

The curable composition of the present invention may contain components other than those described above as appropriate according to the purpose as long as such components do not impair a function as the curable composition.

For example, the curable composition of the present invention may contain various stabilizers such as a polymerization inhibitor and an ultraviolet absorber in order to enhance storage stability of the polymerizable monomer (C) and the like, and may contain known pigments, dyes, fluorescent agents and the like in order to adjust color tone. In addition, the curable composition may contain a calcium-containing compound such as calcium chloride, a fluorine-containing compound such as sodium fluoride, known biologically active components such as an antifungal agent and an antibacterial agent, and the like. Further, in order to improve strength of the obtained cured product, the curable composition may contain a known reinforcing material such as fiber.

The content of each of the other components is preferably 0.00001 to 20 parts by mass, more preferably 0.00005 to 10 parts by mass, and particularly preferably 0.0001 to 5 part by mass, based on 100 parts by mass of the polymerizable monomer (C) contained in the curable composition of the present invention, from the viewpoint of not impairing the effects of the present invention, and exhibiting characteristics of the other components.

Examples of the form of the curable composition of the present invention include forms such as liquid and paste. The curable composition of the present invention is preferably a paste from the viewpoint of easy handling.

The curing time at 37° C. of the curable composition of the present invention is preferably 0.5 to 5 minutes, more preferably 0.8 to 4 minutes, further preferably 1.0 to 3.0 minutes, and particularly preferably 1.0 to 2.9 minutes. Further, three-point bending strength is preferably 80 MPa or more, more preferably 100 MPa or more, and further preferably 120 MPa or more.

(Application)

The curable composition of the present invention can be suitably used as a dental material. Examples thereof include dental adhesives, dental filler materials, dental sealant (tooth fovea fissure sealant), core build-up materials, denture base resins, denture base lining materials, crown prosthetic resins (hard resins for crowns), dental room-temperature polymerization resins, and the like.

Examples of the dental adhesive include dental adhesive resin cements, orthodontic adhesives, mobile tooth fixing adhesives, adhesives for application to cavity, dental bonding materials, and the like.

Examples of the dental filler material include dental composite resins (including dental self-adhesive composite resins), root canal fillers, temporary sealing materials, backing materials, and the like.

Of these, the curable composition of the present invention is suitable for a dental filler material in that it is excellent in bending strength, bending elastic modulus, and adhesion to tooth.

The curable composition of the present invention can be used by a method generally used as the dental material. For example, when the curable composition of the present invention is used as a dental adhesive resin cement, it can be used by a method of subjecting an adhesive surface such as enamel and a metal surface to treatment such as washing with water and drying, then preparing an adhesive liquid obtained by mixing resin cement powder and the curable composition of the present invention, applying the adhesive liquid to a tooth surface, and adhering a bracket, or the like.

For example, when the curable composition of the present invention is used as a root canal filler, it can be used by a method of removing adhesion inhibitors such as NaOCl adhered in a root canal and removing a smear layer adhered to a root canal wall, preparing a sealer-mixed mud in which the curable composition of the present invention and a powder material for sealer are mixed, transferring it to a root canal, filling it, and curing it at a predetermined temperature, or the like.

For example, when the curable composition of the present invention is used as a composite resin for filling and restoration, it can be used in a method of subjecting a formed cavity to dental pulp protection, a bonding treatment, and the like, and then filling to the cavity a paste in which the curable composition of the present invention and a powder such as silica are mixed, and, for example, irradiating light of a predetermined wavelength for a predetermined time to cure the paste, or the like.

<Kit for Preparing Curable Composition>

Another embodiment of the present invention, a kit for preparing a curable composition is composed of a first pack containing the compound (A), a second pack containing the transition metal compound (B), and the like, and the polymerizable monomer (C) is contained in one or both of the first pack and the second pack.

In the presence of the polymerizable monomer (C), when the compound (A) in the first pack and the transition metal compound (B) in the second pack are mixed, polymerization starts. Therefore, sufficient operation time and appropriate curing time can be secured by storing separately the compound (A) and the transition metal compound (B), and mixing these when curing the curable composition.

The first pack may contain, in addition to the compound (A), the polymerizable monomer (C), peroxide (D), filler (E), reducing agent (F), aqueous solvent (G) and photopolymerization initiator (H) described above, and a polymerization inhibitor, and the like. These components may be used singly or in combination of two or more thereof.

The second pack may contain, in addition to the transition metal compound (B), the polymerizable monomer (C), peroxide (D), filler (E), reducing agent (F), aqueous solvent (G) and photopolymerization initiator (H) described above, and a polymerization inhibitor, and the like. These components may be used singly or in combination of two or more thereof.

From the viewpoint of reactivity with the compound (A), when camphorquinone is contained as the photopolymerization initiator (H), the camphorquinone is preferably contained in the second pack rather than the first pack. Moreover, from the viewpoint of reactivity with the transition metal compound (B), the reducing agent (F) and the peroxide (D) are preferably contained in the first pack rather than the second pack. When used as the photopolymerization initiator (H), the aromatic amine compound may be added to either the first pack or the second pack.

The total content of the polymerizable monomer (C) in the first pack and the second pack is, like the curable composition of the present invention, preferably 100 to 200,000 parts by mass, more preferably 500 to 100,000 parts by mass, and more preferably 1,000 to 50,000 parts by mass, based on 100 parts by mass of the compound (A) in the first pack. The total content of other components in the first pack and the second pack is also the same as that of the curable composition of the present invention.

The kit for preparing a curable composition of the present invention can be used by a method generally known as a dental material as described above. For example, when used as a dental filler material, for example, it can be used in a method of removing adhesion inhibitors such as NaOCl adhered in a root canal and removing a smear layer adhered to a root canal wall, then preparing a mixed mud in which the first pack and the second pack, and a powder material for sealer are mixed in a container, transferring it to a root canal, filling it, and curing it at a predetermined temperature, or the like.

The kit for preparing a curable composition of the present invention may contain, in addition to the first pack and the second pack, equipment, a pretreatment agent and the like according to the purpose. For example, when used as a root canal filler, a pottery or a container made of aluminum or the like used for mixing the first pack and the second pack, a dental spatula used for mixing, a brush handle made of aluminum alloy, pretreatment agents for removing adhesion inhibitors and for removing a smear layer and the like may be included in the kit.

Examples

Hereinafter, the present invention will be described in detail with reference to examples and comparative examples, but the present invention is not limited to these examples. Abbreviations for compounds used in examples are shown below.

[Pyrazolidinedione Compound and/or Pyrazolidine(Di)Thione Compound (A1)]

PBZ: Phenylbutazone (manufactured by Tokyo Chemical Industry Co., Ltd.)

[Salt of Pyrazolidinedione Compound and/or Salt (A2) of Pyrazolidine(Di)Thione Compound]

PBZCa: Phenylbutazone calcium (manufactured by Woongjin Chemical Co., Ltd.)

PBZNa: Phenylbutazone sodium (manufactured by Woongjin Chemical Co., Ltd.)

[Malonate Compound (A3)]

DEPM: Diethyl phenylmalonate (manufactured by Tokyo Chemical Industry Co., Ltd.)

TEMTC: Triethyl methanetricarboxylate (manufactured by Tokyo Chemical Industry Co., Ltd.)

[Transition Metal Compound (B)]

$CuCl_2$: Copper(II) chloride (manufactured by FUJIFILM Wako Pure Chemical Corporation)

$Cu(acac)_2$: Copper acetylacetonate (manufactured by Tokyo Chemical Industry Co., Ltd.)

[Polymerizable Monomer (C)]

UDMA: 1,6-Bis(methacryloxyethyloxycarbonylamino)-2,2,4-trimethylhexane (a compound synthesized by reacting 2,2,4-trimethylhexyl diisocyanate (TMHDI, Tokyo Chemical Industry Co., Ltd.) and 2-hydroxyethyl methacrylate (HEMA, Mitsubishi Chemical Corporation) at a ratio of 1:2, according to a known urethanization reaction method)

Bis-GMA: Bisphenol A diglycidyl methacrylate (manufactured by Shin-Nakamura Chemical Co, Ltd.)

NBDI-HEA: A compound synthesized by reacting a mixture (NBDI, manufactured by Mitsui Chemicals, Inc.) of 2,5-bis(isocyanatomethyl)bicyclo[2.2.1]heptane and 2,6-bis(isocyanatomethyl)bicyclo[2.2.1]heptane with 2-hydroxyethyl acrylate (HEA, manufactured by Nippon Shokubai Co., Ltd.) at a ratio of 1:2, according to a known urethanization reaction method.

TEGDMA: Triethylene glycol dimethacrylate (manufactured by Shin-Nakamura Chemical Co, Ltd.)

HexDMA: 1,6-hexanediol dimethacrylate (manufactured by Shin-Nakamura Chemical Co, Ltd.)

GDMA: Glycerol dimethacrylate (manufactured by Shin-Nakamura Chemical Co, Ltd.)

HEMA: 2-Hydroxyethyl methacrylate (manufactured by Mitsubishi Chemical Corporation)

4-MET: 4-Methacryloyloxyethyl trimellitic acid (obtained by adding 1.2 equivalents of pure water to 4-methacryloyloxyethyl trimellitic anhydride (4-META, manufactured by FUJIFILM Wako Pure Chemical Corporation) and stirring the mixture overnight, and then pulverizing the mixture)

MDP: 10-Methacryloyloxydecyl dihydrogen phosphate (manufactured by FUJIFILM Wako Pure Chemical Corporation) [Peroxide (D)]

tBPB: t-Butyl peroxybenzoate (trade name "Luperox P", manufactured by Sigma-Aldrich Co. Ltd.)

tAPiN: t-Amyl peroxyisononanoate (trade name "Luperox 570", manufactured by ARKEMA Yoshitomi, Ltd.)

TMBHP: 1,1,3,3-Tetramethylbutyl hydroperoxide (trade name "Luperox 215", manufactured by ARKEMA Yoshitomi, Ltd.)

tBPCy: 1,1-Di(t-butylperoxy)cyclohexane (trade name "Luperox 331XL", manufactured by ARKEMA Yoshitomi, Ltd.)

BPO: Benzoyl peroxide (manufactured by Tokyo Chemical Industry Co., Ltd.)

[Filler (E)]

GM27884: Silane-treated barium glass powder (trade name "GM27884", manufactured by SCHOTT, particle size 1.5 μm, treated with γ-MPTS at 1.6% based on filler weight)

8235: Silane-treated barium glass powder (trade name "8235", manufactured by SCHOTT, particle size 0.7 μm, treated with γ-MPTS at 6% based on filler weight))

R812: Fine particle silica (trade name "AEROSIL R812", manufactured by Nippon Aerosil Co., Ltd.)

[Reducing Agent (F)]

p-TSS: Sodium p-toluenesulfinate (manufactured by FUJIFILM Wako Pure Chemical Corporation, dried at 70° C. under reduced pressure after purchase, and pulverized by a mortar)

DEPT: N,N-Diethanol-p-toluidine (manufactured by FUJIFILM Wako Pure Chemical Corporation)

[Aqueous Solvent (G)]

Acetone: Acetone (manufactured by FUJIFILM Wako Pure Chemical Corporation)

EtOH: Ethanol (manufactured by FUJIFILM Wako Pure Chemical Corporation)

Distilled water: manufactured using a distilled water production equipment (manufactured by Tokyo Rikakikai Co., Ltd.)

[Photopolymerization Initiator (H)]

CQ: d,l-Camphorquinone (manufactured by FUJIFILM Wako Pure Chemical Corporation)

DMABAE: Ethyl N,N-dimethylaminobenzoate (manufactured by FUJIFILM Wako Pure Chemical Corporation)

TPO: 2,4,6-Trimethylbenzoyl-diphenyl-phosphine oxide (trade name "Irgacure TPO", manufactured by BASF Corporation) [Other components: Polymerization inhibitor]

BHT: 2,6-Di-t-butyl-4-methylphenol (manufactured by Tokyo Chemical Industry Co., Ltd.)

MEHQ: 4-Methoxyphenol (manufactured by FUJIFILM Wako Pure Chemical Corporation)

<Preparation of First Pack and Second Pack for Preparing Curable Composition>

Paste-like first pack and second pack to be used for preparing the curable compositions of examples and comparative examples were prepared by blending and mixing components in proportions (parts by mass) shown in Table 1.

<Measurement Method of Curing Time>

The curing time in examples and comparative examples shown in Tables 1 and 2 were measured by differential thermal analysis using a differential scanning calorimeter (DSC). As the measuring apparatus, a DSC 3500 Sirius (manufactured by NETZSCH) was used.

Specifically, the first pack and the second pack taken in equal amounts were mixed on a dental kneading paper with a dental spatula for 10 seconds at room temperature set to 20 to 25° C. to obtain a polymerizable mixture. The obtained polymerizable mixture was filled in a sample pan made of Al for DSC measurement.

The sample pan made of Al filled with the polymerizable mixture was placed in a DSC thermostat set at 37±1° C. just before measurement, and measurement was started seconds after the start of kneading. The time until the point at which the temperature rises due to the start of the curing reaction of the polymerizable mixture and reached the maximum temperature was recorded as the curing time.

<Measurement Method of Pot Life>

Equal amounts of the first pack and the second pack of the composition shown in Table 3 were taken on a dental kneading paper, and kneaded with a dental spatula at experimental room temperature, and a time until curing behavior could be confirmed was recorded and defined as a pot life. The time measurement was started at the same time as the start of kneading.

<Measurement Method of Three-Point Bending Strength>

The first pack and the second pack shown in Tables 1 to 3 taken in equal amounts were mixed on a dental kneading paper with a dental spatula for 10 seconds at room temperature set to 20 to 25° C. to obtain a homogeneous polymerizable mixture. The obtained polymerizable mixture was filled in a 2 mm×2 mm×25 mm mold for test piece preparation, pressed from both sides with a Lumirror film, and polymerized in a thermostat set to 37±1° C. for 1 hour, and the obtained cured body was used as a test piece.

When preparing a test piece by chemical polymerization, a cured body obtained by polymerization in a mold filled with the mixture within a thermostat set to 37±1° C. for 1 hour was used as a test piece.

When preparing a test piece by photopolymerization, a cured body obtained by irradiating with light on back and front for 1 minute and 30 seconds using a technical LED irradiator was used as a test piece.

In addition, "LC mode" and values marked with an asterisk (*) in Tables 1 to 3 show a case where a test piece was prepared by photopolymerization and measurement results of three-point bending strength and bending elastic modulus of the test piece.

Each test piece was removed from the mold, immersed in distilled water, stored in a thermostat set to 37±1° C. for 18 hours. The test piece was then taken out, and a three-point bending test was performed using a universal testing machine (manufactured by Intesco Co., Ltd.). The test was performed by applying a load until the test piece broke at a crosshead speed of 1 ram/min, and the strength of the cured body was calculated from the obtained maximum point stress. At that time, the bending elastic modulus was also calculated.

As shown in Table 1, Comparative Example 1 containing no PBZ had a curing time of 3 minutes or more and sufficient polymerization properties were not obtained, whereas Examples 1 to 11 all had a curing time in the range of 1 minute or more and less than 3 minutes, which was appropriate curing time. In addition, Examples 1 to 11 were excellent in bending strength and bending elastic modulus, whereas Comparative Examples 1 and 2 were insufficient in polymerization properties and sufficient bending strength and bending elastic modulus were not also obtained. Furthermore, in Example 11, it was also possible to use a CQ-based photopolymerization initiator in combination.

As shown in Table 2, Examples 14 to 26 containing PBZCa or PBZNa all had a curing time in the range of 1 minute or more and less than 3 minutes, which was appropriate curing time. Further, Examples 14 to 26 were excellent in bending strength and bending elastic modulus. On the other hand, Comparative Examples 1 and 2 containing no PBZCa and PBZNa had a curing time of 3 minutes or more and had insufficient polymerization properties, and sufficient bending strength and bending elastic modulus were not also obtained. Further, in Examples 25 and 26, it was also possible to use a CQ-based or TPO-based photopolymerization initiator in combination.

On the other hand, as shown in Tables 1 and 2, Comparative Example 2 and Comparative Example 3 are both compositions containing a BPO-aromatic amine compound (DEPT) polymerization initiator system, and Comparative Example 3 contains a larger amount of DEPT than Comparative Example 2. Even though sufficient polymerization properties were not obtained in Comparative Example 2, in Comparative Example 3 in which the amount of DEPT was increased, the curing time was improved to some extent, and the bending strength and bending elastic modulus were improved, but a yellowed cured body was obtained.

Based on this, it was found that a polymerization initiator system utilizing PBZ or a salt of PBZ and a transition metal compound is a polymerization initiator system excellent in curing time, bending strength and bending elastic modulus while suppressing discoloration due to an amine compound.

Although not shown in Table 1, as Example 12 or Example 13, when the first pack and the second pack were prepared in the same formulation as in Example 2, except for using 3 parts by mass of DEPM (Example 12) or 3 parts by mass of TEMTC (Example 13) as a malonate compound (A3) instead of 1 part by mass of PBZ contained in the first pack, and the curing time was measured for Example 12 or Example 13 as well, the curing time of Example 12 was 2.4 minutes and the curing time of Example 13 was 2.6 minutes. From this result, it was shown that the curing time was excellent by utilizing the malonate compound.

When the pot life was evaluated in Examples 27 to 37 shown in Table 3, it was in the range of 1 minute or more and less than 3 minutes, and it was found that they have an appropriate length of pot life. On the other hand, Comparative Examples 4 and 5 containing no PBZ and a PBZ salt, and Comparative Example 6 constituted by BPO/aromatic amine chemical polymerization system did not show sufficient polymerization properties.

Further, the curable compositions of Examples 27 to 37 showed excellent three-point bending strength and bending elastic modulus.

From the above, when the curing time is in the range of 1 minute to less than 3 minutes in the curing time measurement, or when the pot life was in the range of 1 minute to less than 3 minutes in the pot life measurement, it can be determined that the evaluated curable composition has an appropriate curability. Further, when the three-point bending strength of the obtained cured product is 80 MPa or more, it can be determined that the polymerization initiator of the present invention gives a cured product having sufficient strength.

TABLE 1

|  |  | Example 1 | Example 2 | Example 3 | Example 4 | Example 5 | Example 6 | Example 7 | Example 8 |
|---|---|---|---|---|---|---|---|---|---|
| First Pack | UDMA | 70 | 70 | 70 | 70 | 70 | 70 | 70 | — |
|  | NBDI-HEA | — | — | — | — | — | — | — | 70 |
|  | TEGDMA | 30 | 30 | 30 | 30 | 30 | 30 | 30 | 30 |
|  | PBZ | 1 | 1 | 1 | 1 | 1 | 1 | 1 | 1 |
|  | TMBHP | 1 | — | — | 1 | — | — | — | — |
|  | tBPB | — | 1 | — | — | 1 | — | — | 2 |
|  | tBPCy | — | — | 5 | — | — | 3 | 5 | — |
|  | BPO | — | — | — | — | — | — | — | — |
|  | BHT | 0.2 | 0.2 | 0.2 | 0.2 | 0.2 | 0.2 | 0.2 | 0.2 |
|  | MEHQ | 0.1 | 0.1 | 0.1 | 0.1 | 0.1 | 0.1 | 0.1 | 0.1 |
|  | R812 | 10 | 10 | 10 | 10 | 10 | 10 | 10 | 10 |
|  | 8235 | 70 | 70 | 70 | 70 | 70 | 70 | 70 | 70 |
|  | GM27884 | 150 | 150 | 150 | 150 | 150 | 150 | 150 | 150 |
| Second Pack | UDMA | 70 | 70 | 70 | 70 | 70 | 70 | 70 | 70 |
|  | Bis-GMA | — | — | — | — | — | — | — | — |
|  | TEGDMA | 30 | 30 | 30 | — | — | — | — | — |
|  | GDMA | — | — | — | 30 | 30 | 30 | 30 | 30 |
|  | $CuCl_2$ | 0.1 | 0.1 | 0.1 | 0.1 | 0.05 | 0.1 | 0.1 | 0.1 |
|  | CQ | — | — | — | — | — | — | — | — |
|  | DMABAE | — | — | — | — | — | — | — | — |
|  | DEPT | — | — | — | — | — | — | — | — |
|  | BHT | 0.2 | 0.2 | 0.2 | 0.2 | 0.2 | 0.2 | 0.2 | 0.2 |
|  | MEHQ | 0.1 | 0.1 | 0.1 | 0.1 | 0.1 | 0.1 | 0.1 | 0.1 |
|  | R812 | 10 | 10 | 10 | 10 | 10 | 10 | 10 | 10 |
|  | 8235 | 70 | 70 | 70 | 70 | 70 | 70 | 70 | 70 |
|  | GM27884 | 150 | 150 | 150 | 150 | 150 | 150 | 150 | 150 |
| Evaluation Results | Curing time | 2.3 min | 2.4 min | 2.3 min | 1.1 min | 1.2 min | 2.0 min | 1.7 min | 1.5 min |
|  | Three-point bending strength (SD) | 135.4 MPa (SD 14.1) | 132.9 MPa (SD 4.4) | 124.0 MPa (SD 0.7) | 136.1 MPa (SD 0.8) | 133.5 MPa (SD 7.8) | 133.2 MPa (SD 19.8) | 168.4 MPa (SD 12.7) | 129.6 MPa (SD 11.4) |
|  | Bending elastic modulus (SD) | 6.9 GPa (SD 0.7) | 5.2 GPa (SD 0.9) | 5.4 GPa (SD 0.5) | 6.5 GPa (SD 0.6) | 7.4 GPa (SD 0.5) | 7.6 GPa (SD 0.5) | 7.9 GPa (SD 0.1) | 6.9 GPa (SD 0.3) |

|  |  | Example 9 | Example 10 | Example 11 | Comparative Example 1 | Comparative Example 2 | Comparative Example 3 |
|---|---|---|---|---|---|---|---|
| First Pack | UDMA | 70 | 70 | 70 | 70 | 70 | 70 |
|  | NBDI-HEA | — | — | — | — | — | — |
|  | TEGDMA | 30 | 30 | 30 | 30 | 30 | 30 |
|  | PBZ | 1 | 1 | 1 | — | — | — |
|  | TMBHP | — | — | — | — | — | — |
|  | tBPB | 1 | 3 | 1 | 1 | — | — |
|  | tBPCy | — | — | — | — | — | — |
|  | BPO | — | — | — | — | 3 | 3 |
|  | BHT | 0.2 | 0.2 | 0.2 | 0.2 | 0.2 | 0.2 |

TABLE 1-continued

|  |  |  |  |  |  |  |  |
|---|---|---|---|---|---|---|---|
|  | MEHQ | 0.1 | 0.1 | 0.1 | 0.1 | 0.1 | 0.1 |
|  | R812 | 10 | 10 | 10 | 10 | 10 | 10 |
|  | 8235 | 70 | 70 | 70 | 70 | 70 | 70 |
|  | GM27884 | 150 | 150 | 150 | 150 | 150 | 150 |
| Second Pack | UDMA | — | — | — | 70 | 70 | 70 |
|  | Bis-GMA | 70 | 70 | 70 | — | — | — |
|  | TEGDMA | 30 | 30 | 30 | 30 | 30 | 30 |
|  | GDMA | — | — | — | — | — | — |
|  | CuCl$_2$ | 0.001 | 0.001 | 0.001 | 0.1 | — | — |
|  | CQ | — | — | 0.1 | — | — | — |
|  | DMABAE | — | — | 0.3 | — | — | — |
|  | DEPT | — | — | — | — | 1 | 3 |
|  | BHT | 0.2 | 0.2 | 0.2 | 0.2 | 0.2 | 0.2 |
|  | MEHQ | 0.1 | 0.1 | 0.1 | 0.1 | 0.1 | 0.1 |
|  | R812 | 10 | 10 | 10 | 10 | 10 | 10 |
|  | 8235 | 70 | 70 | 70 | 70 | 70 | 70 |
|  | GM27884 | 150 | 150 | 150 | 150 | 150 | 150 |
| Evaluation Results | Curing time | 13 min | 1.1 min | 1.6 min | LC mode | 8.8 min | >10 min | 3.0 min |
|  | Three-point bending strength (SD) | 160.4 MPa (SD 4.5) | 151.2 MPa (SD 11.6) | 144.0 MPa (SD 8.8) | *148.6 MPa (SD 10.2) | — | — | 122.5 MPa (SD 3.0) |
|  | Bending elastic modulus (SD) | 10.6 GPa (SD 0.2) | 8.8 GPa (SD 0.5) | 8.7 GPa (SD 0.3) | *8.9 GPa (SD 0.6) | — | — | 6.2 GPa (SD 0.2) |

TABLE 2

|  |  | Example 14 | Example 15 | Example 16 | Example 17 | Example 18 | Example 19 | Example 20 | Example 21 | Example 22 | Example 23 |
|---|---|---|---|---|---|---|---|---|---|---|---|
| First Pack | UDMA | 70 | 70 | 70 | 70 | 70 | 70 | 70 | 70 | 70 | 70 |
|  | TEGDMA | 30 | 30 | 30 | 30 | 30 | 30 | 30 | 30 | 30 | — |
|  | HexDMA | — | — | — | — | — | — | — | — | — | 30 |
|  | PBZCa | 5 | 1 | 1 | 1 | — | — | — | 5 | 1 | 1 |
|  | PBZNa | — | — | — | — | 1 | 1 | 1 | — | — | — |
|  | tBPB | 1 | 1 | 1 | 5 | 1 | 1 | 5 | — | — | 1 |
|  | tAPiN | — | — | — | — | — | — | — | 5 | 5 | — |
|  | BPO | — | — | — | — | — | — | — | — | — | — |
|  | TPO | — | — | — | — | — | — | — | — | — | — |
|  | BHT | 0.2 | 0.2 | 0.2 | 0.2 | 0.2 | 0.2 | 0.2 | 0.2 | 0.2 | 0.2 |
|  | MEHQ | 0.1 | 0.1 | 0.1 | 0.1 | 0.1 | 0.1 | 0.1 | 0.1 | 0.1 | 0.1 |
|  | R812 | 10 | 10 | 10 | 10 | 10 | 10 | 10 | 10 | 10 | 10 |
|  | 8235 | 70 | 70 | 70 | 70 | 70 | 70 | 70 | 70 | 70 | 70 |
|  | GM27884 | 150 | 150 | 150 | 150 | 150 | 150 | 150 | 150 | 150 | 150 |
| Second Pack | UDMA | 70 | 70 | — | 70 | 70 | — | — | — | — | 70 |
|  | Bis-GMA | — | — | 70 | — | — | 70 | 70 | 70 | 70 | — |
|  | TEGDMA | 30 | — | 30 | — | — | 30 | 30 | 30 | 30 | — |
|  | GDMA | — | 30 | — | 30 | 30 | — | — | — | — | 30 |
|  | CuCl$_2$ | 0.1 | 0.1 | 0.001 | 0.1 | 0.1 | 0.005 | 0.001 | 0.001 | 0.001 | 0.1 |
|  | DEPT | — | — | — | — | — | — | — | — | — | — |
|  | CQ | — | — | — | — | — | — | — | — | — | — |
|  | DMABAE | — | — | — | — | — | — | — | — | — | — |
|  | BHT | 0.2 | 0.2 | 0.2 | 0.2 | 0.2 | 0.2 | 0.2 | 0.2 | 0.2 | 0.2 |
|  | MEHQ | 0.1 | 0.1 | 0.1 | 0.1 | 0.1 | 0.1 | 0.1 | 0.1 | 0.1 | 0.1 |
|  | R812 | 10 | 10 | 10 | 10 | 10 | 10 | 10 | 10 | 10 | 10 |
|  | 8235 | 70 | 70 | 70 | 70 | 70 | 70 | 70 | 70 | 70 | 70 |
|  | GM27884 | 150 | 150 | 150 | 150 | 150 | 150 | 150 | 150 | 150 | 150 |
| Evaluation Results | Curing time | 2.9 min | 1.8 min | 1.5 min | 1.6 min | 1.0 min | 1.2 min | 2.2 min | 1.2 min | 2.5 min | 2.0 min |
|  | Three-point bending strength (SD) | 130.6 MPa (SD 11.1) | 134.8 MPa (SD 11.7) | 144.2 MPa (SD 10.5) | 126.0 MPa (SD 8.4) | 136.2 MPa (SD 6.4) | 133.3 MPa (SD 4.7) | 134.9 MPa (SD 4.4) | 125.5 MPa (SD 15.8) | 134.7 MPa (SD 7.8) | 123.5 MPa (SD 8.1) |
|  | Bending elastic modulus (SD) | 6.8 GPa (SD 0.3) | 6.6 GPa (SD 0.4) | 7.8 GPa (SD 0.3) | 5.8 GPa (SD 0.4) | 6.4 GPa (SD 0.4) | 7.6 GPa (SD 0.2) | 6.6 GPa (SD 0.4) | 6.5 GPa (SD 0.3) | 6.7 GPa (SD 0.9) | 5.9 GPa (SD 0.1) |

|  |  | Example 24 | Example 25 | Example 26 | Comparative Example 1 | Comparative Example 2 | Comparative Example 3 |
|---|---|---|---|---|---|---|---|
| First Pack | UDMA | 70 | 70 | 70 | 70 | 70 | 70 |
|  | TEGDMA | — | 30 | 30 | 30 | 30 | 30 |
|  | HexDMA | 30 | — | — | — | — | — |
|  | PBZCa | 1 | 5 | 5 | — | — | — |
|  | PBZNa | — | — | — | — | — | — |
|  | tBPB | 1 | 1 | 1 | 1 | — | — |

TABLE 2-continued

|  |  |  |  |  |  |  |  |
|---|---|---|---|---|---|---|---|
|  | tAPiN | — | — | — | — | — | — |
|  | BPO | — | — | — | — | 3 | 3 |
|  | TPO | — | 0.5 | — | — | — | — |
|  | BHT | 0.2 | 0.2 | 0.2 | 0.2 | 0.2 | 0.2 |
|  | MEHQ | 0.1 | 0.1 | 0.1 | 0.1 | 0.1 | 0.1 |
|  | R812 | 10 | 10 | 10 | 10 | 10 | 10 |
|  | 8235 | 70 | 70 | 70 | 70 | 70 | 70 |
|  | GM27884 | 150 | 150 | 150 | 150 | 150 | 150 |
| Second Pack | UDMA | — | 70 | 70 | 70 | 70 | 70 |
|  | Bis-GMA | 70 | — | — | — | — | — |
|  | TEGDMA | 30 | 30 | 30 | 30 | 30 | 30 |
|  | GDMA | — | — | — | — | — | — |
|  | $CuCl_2$ | 0.005 | 0.1 | 0.1 | 0.1 | — | — |
|  | DEPT | — | — | — | — | 1 | 3 |
|  | CQ | — | — | 0.1 | — | — | — |
|  | DMABAE | — | — | 0.3 | — | — | — |
|  | BHT | 0.2 | 0.2 | 0.2 | 0.2 | 0.2 | 0.2 |
|  | MEHQ | 0.1 | 0.1 | 0.1 | 0.1 | 0.1 | 0.1 |
|  | R812 | 10 | 10 | 10 | 10 | 10 | 10 |
|  | 8235 | 70 | 70 | 70 | 70 | 70 | 70 |
|  | GM27884 | 150 | 150 | 150 | 150 | 150 | 150 |
| Evaluation Results | Curing time | 1.0 min | 1.5 min | LC mode | 1.5 min | LC mode | 8.8 min | >10 min | 3.0 min |
|  | Three-point bending strength (SD) | 144.1 MPa (SD 3.6) | 132.4 MPa (SD 7.3) | *129.5 MPa (SD 1.1) | 139.6 MPa (SD 13.4) | *155.0 MPa (SD 4.2) | — | — | 122.5 MPa (SD 3.0) |
|  | Bending elastic modulus (SD) | 6.6 GPa (SD 0.2) | 6.9 GPa (SD 0.0) | *7.3 GPa (SD 0.1) | 7.2 GPa (SD 0.3) | *7.9 GPa (SD 0.2) | — | — | 6.2 GPa (SD 0.2) |

TABLE 3

|  |  | Example 27 | Example 28 | Example 29 | Example 30 | Example 31 | Example 32 | Example 33 | Example 34 |
|---|---|---|---|---|---|---|---|---|---|
| First Pack | UDMA | 70 | 70 | 70 | 70 | 70 | 70 | 70 | 70 |
|  | TEGDMA | 30 | 30 | 30 | 30 | 30 | 30 | 30 | 30 |
|  | PBZ | 2 | 2 | 2 | 2 | 2 | 2 | — | — |
|  | PBZCa | — | — | — | — | — | — | 1 | 1 |
|  | tBPB | 0.5 | — | 0.5 | 0.5 | 0.5 | — | 0.5 | 0.5 |
|  | tAPiN | — | 0.5 | — | — | — | 0.5 | — | — |
|  | DEPT | — | — | — | — | — | — | — | — |
|  | DMABAE | — | — | — | — | — | — | — | — |
|  | p-TSS | 2 | 2 | 2 | 2 | 2 | 2 | 2 | 2 |
|  | BHT | 0.2 | 0.2 | 0.2 | 0.2 | 0.2 | 0.2 | 0.2 | 0.2 |
|  | MEHQ | 0.1 | 0.1 | 0.1 | 0.1 | 0.1 | 0.1 | 0.1 | 0.1 |
|  | R812 | 10 | 10 | 10 | 10 | 10 | 10 | 10 | 10 |
|  | GM27884 | 70 | 70 | 70 | 70 | 70 | 70 | 70 | 70 |
|  | 8235 | 70 | 70 | 70 | 70 | 70 | 70 | 70 | 70 |
| Second Pack | UDMA | 60 | 60 | 60 | — | 35 | 35 | 60 | — |
|  | Bis-GMA | — | — | — | 60 | 35 | 35 | — | 60 |
|  | TEGDMA | 20 | 20 | 20 | 20 | 25 | 25 | 20 | 20 |
|  | GDMA | — | — | 20 | — | — | — | — | — |
|  | 4-MET | 20 | 20 | 20 | — | 5 | 5 | 20 | — |
|  | MDP | — | — | — | 20 | — | — | — | 20 |
|  | $Cu(acac)_2$ | 0.01 | 0.01 | 0.02 | 0.002 | 0.002 | 0.002 | 0.02 | 0.002 |
|  | CQ | — | — | — | — | — | — | — | — |
|  | BPO | — | — | — | — | — | — | — | — |
|  | BHT | 0.2 | 0.2 | 0.2 | 0.2 | 0.2 | 0.2 | 0.2 | 0.2 |
|  | MEHQ | 0.1 | 0.1 | 0.1 | 0.1 | 0.1 | 0.1 | 0.1 | 0.1 |
|  | R812 | 10 | 10 | 10 | 10 | 10 | 10 | 10 | 10 |
|  | GM27884 | 70 | 70 | 70 | 70 | 70 | 70 | 70 | 70 |
|  | 8235 | 70 | 70 | 70 | 70 | 70 | 70 | 70 | 70 |
| Evaluation Results | Pot life | 1.5 min | 1.5 min | 1.8 min | 2.3 min | 1.0 min | 1.5 min | 1.8 min | 2.3 min |
|  | Three-point bending strength (SD) | 129.4 MPa (SD 0.4) | 117.6 MPa (SD 3.9) | 125.9 MPa (SD 11.4) | 133.5 MPa (SD 3.6) | 130.1 MPa (SD 7.0) | 134.7 MPa (SD 9.3) | 124.4 MPa (SD 4.1) | 107.0 MPa (SD 20.4) |
|  | Bending elastic modulus (SD) | 6.0 GPa (SD 0.5) | 5.9 GPa (SD 0.3) | 7.0 GPa (SD 0.1) | 6.3 GPa (SD 0.2) | 7.0 GPa (SD 0.2) | 6.2 GPa (SD 0.1) | 5.6 GPa (SD 0.3) | 5.9 GPa (SD 0.2) |

TABLE 3-continued

|  |  | Example 35 | Example 36 | Example 37 |  | Comparative Example 4 | Comparative Example 5 | Comparative Example 6 |
|---|---|---|---|---|---|---|---|---|
| First Pack | UDMA | 70 | 70 | 70 |  | 70 | 70 | 70 |
|  | TEGDMA | 30 | 30 | 30 |  | 30 | 30 | 30 |
|  | PBZ | — | 2 | — |  | — | — | — |
|  | PBZCa | 1 | — | 1 |  | — | — | — |
|  | tBPB | 0.5 | 0.5 | 0.5 |  | 0.5 | — | — |
|  | tAPiN | — | — | — |  | — | — | — |
|  | DEPT | — | — | — |  | — | — | 0.5 |
|  | DMABAE | — | 0.3 | 0.3 |  | — | — | — |
|  | p-TSS | 2 | 2 | 2 |  | 2 | 2 | 5 |
|  | BHT | 0.2 | 0.2 | 0.2 |  | 0.2 | 0.2 | 0.2 |
|  | MEHQ | 0.1 | 0.1 | 0.1 |  | 0.1 | 0.1 | 0.1 |
|  | R812 | 10 | 10 | 10 |  | 10 | 10 | 10 |
|  | GM27884 | 70 | 70 | 70 |  | 70 | 70 | 70 |
|  | 8235 | 70 | 70 | 70 |  | 70 | 70 | 70 |
| Second Pack | UDMA | 35 | 60 | 60 |  | 60 | 60 | 60 |
|  | Bis-GMA | 35 | — | — |  | — | — | — |
|  | TEGDMA | 25 | 20 | 20 |  | 20 | 20 | 20 |
|  | GDMA | — | — | — |  | — | — | — |
|  | 4-MET | 5 | 20 | 20 |  | 20 | 20 | 20 |
|  | MDP | — | — | — |  | — | — | — |
|  | Cu (acac)$_2$ | 0.002 | 0.01 | 0.02 |  | 0.01 | 0.01 | — |
|  | CQ | — | 0.05 | 0.1 |  | — | — | — |
|  | BPO | — | — | — |  | — | — | 1 |
|  | BHT | 0.2 | 0.2 | 0.2 |  | 0.2 | 0.2 | 0.2 |
|  | MEHQ | 0.1 | 0.1 | 0.1 |  | 0.1 | 0.1 | 0.1 |
|  | R812 | 10 | 10 | 10 |  | 10 | 10 | 10 |
|  | GM27884 | 70 | 70 | 70 |  | 70 | 70 | 70 |
|  | 8235 | 70 | 70 | 70 |  | 70 | 70 | 70 |
| Evaluation Results | Pot life | 1.7 min | 1.8 min | 2.1 min | LC mode | >10 min | 3.8 min | 4.0 min |
|  | Three-point bending strength (SD) | 134.5 MPa (SD 3.2) | 119.7 MPa (SD 5.2) | 127.7 MPa (SD 13.9) | *129.4 MPa (SD 11.1) / *130.0 MPa (SD 8.0) | — | 55.3 MPa (SD 3.4) | 114.0 MPa (SD 5.0) |
|  | Bending elastic modulus (SD) | 6.6 GPa (SD 0.3) | 6.0 GPa (SD 0.1) | 6.0 GPa (SD 0.1) | *6.1 GPa (SD 0.2) / *6.1 GPa (SD 0.2) | — | 1.9 GPa (SD 0.2) | 5.7 GPa (SD 0.2) |

35

<Evaluation Method of Adhesive Strength to Tooth>

A bovine tooth adherend was removed, then frozen and preserved bovine mandibular anterior teeth were thawed under water injection, and their roots were cut and demyelinated. This was placed in a plastic cylindrical container with a diameter of 25 mm and a depth of 25 mm and embedded in an acrylic resin. Immediately before use, the bovine tooth adherend was polished with water-resistant emery paper (P400), and smooth surfaces of bovine tooth enamel and bovine tooth dentin were carved and used. Measurement was carried out with test pieces used for measuring adhesive strength according to technical standards corresponding to compositions shown in Table 4 or Table 5 (described below). A shear load was applied at a crosshead speed of 1.0 ram/min, in parallel to bovine tooth enamel or dentin surface and in contact with the surface, and the adhesive strength was determined by a shear load when a cured product formed into a column on the bovine tooth surface peels from the surface.

Compressed air was blown onto an adhered surface of the test piece to dry it. After that, equal amounts of the first pack and the second pack described in Table 4 were taken in a dappen, and a curable composition obtained by mixing them was applied to a flat surface of enamel or dentin, and after 20 seconds, a volatile solvent contained in the composition was distilled off with an air syringe. Thereafter, a plastic mold with a diameter of 2.38 mm (manufactured by Ultradent Japan K.K.) was installed, a photopolymerizable material (Fantasista V, manufactured by Sun Medical Company, Ltd) was filled therein, and a cylindrical column was cured by irradiating with light for 20 seconds using a LED visible light irradiator (Translux 2Wave, manufactured by Kulzer GmbH). Then, after immersion in water and storage in a 37° C. thermostat for 18 hours, the adhesive strength was measured.

TABLE 4

|  |  | Example 38 | Example 39 | Example 40 | Example 41 | Example 42 | Example 43 | Example 44 |
|---|---|---|---|---|---|---|---|---|
| Second Pack | UDMA | 50 | 50 | — | — | — | — | — |
|  | Bis-GMA | — | — | 50 | 50 | 50 | 60 | 65 |
|  | GDMA | 10 | — | — | — | — | — | — |
|  | TEGDMA | — | 20 | 20 | 20 | — | 20 | 25 |
|  | HEMA | 10 | — | — | — | 20 | — | — |
|  | MDP | — | — | — | 30 | — | 30 | — |
|  | 4-MET | 30 | 30 | — | 30 | — | 20 | 10 |
|  | CuCl$_2$ | 0.3 | 0.3 | 0.3 | 0.3 | 0.3 | 0.3 | 0.3 |
|  | BHT | 0.1 | 0.1 | 0.1 | 0.1 | 0.1 | 0.1 | 0.1 |
|  | Acetone | — | 70 | 70 | 70 | 70 | 70 | 70 |
|  | H$_2$O | — | 10 | 10 | 10 | 10 | 10 | 10 |

TABLE 4-continued

|  |  | Example 38 | Example 39 | Example 40 | Example 41 | Example 42 | Example 43 | Example 44 |
|---|---|---|---|---|---|---|---|---|
| First Pack | EtOH | 210 | 210 | 210 | 210 | 210 | 210 | 210 |
|  | H2O | 60 | 60 | 60 | 60 | 60 | 60 | 60 |
|  | PBZ | 10 | 10 | 10 | 10 | 10 | 10 | 10 |
|  | p-TSS | 20 | 20 | 20 | 20 | 20 | 20 | 20 |
|  | tBPB | 4 | 4 | 4 | 4 | 4 | 4 | 4 |
|  |  | | | | Adhesion to tooth | | | |
| Bovine tooth enamel | | 10.4 MPa | 10.4 MPa | 17.7 MPa | 13.6 MPa | 12.0 MPa | 14.9 MPa | 12.0 MPa |
| SD | | 2.2 | 1.4 | 3.6 | 2.2 | 2.1 | 3.3 | 3.1 |

A pretreatment material composition (second pack) prepared by the composition of Table 5 was applied to the adhered surface of the bovine dentin dried by blowing compressed air for about 1 second, and after 20 seconds, a solvent component in the composition was distilled off using an air syringe to prepare a primer coating. Next, a paste composition of the prepared first pack was applied to an adherend surface of a cylindrical column cured product (Fantasista V, manufactured by Sun Medical Company, Ltd, one in which an adherend surface was previously polished with water-resistant emery paper P180) of the previously prepared filler composition (first pack), and the cylindrical column cured product was placed on a coating part formed on the bovine dentin tooth adherend, and pressed with a force of 5 N using a dedicated jig. Thereafter, an excess of adapted composition was removed, and the cylindrical column was cured by irradiating using the LED visible light irradiator (Translux 2Wave, manufactured by Kulzer GmbH) from 4 directions for 10 seconds. Then, after immersion in water and storage in a 37° C. thermostat for 18 hours, the adhesive strength was measured.

TABLE 5

|  |  | Example 45 | Example 46 | Example 47 |
|---|---|---|---|---|
| Pretreatment material composition (second pack) | UDMA | 40 | 40 | 40 |
|  | GDMA | 5 | 5 | 5 |
|  | HEMA | 5 | 5 | 5 |
|  | MDP | 20 | 20 | — |
|  | 4-MET | — | — | 20 |
|  | CuCl2 | 1 | 1 | 1 |
|  | BHT | 0.05 | 0.05 | 0.05 |
|  | EtOH | 15 | 15 | 15 |
|  | H2O | 15 | 15 | 15 |
| Filler composition (first pack) | UDMA | 80 | 80 | 80 |
|  | TEGDMA | 20 | 20 | 20 |
|  | CQ | 0.3 | 0.3 | 0.3 |
|  | DMABAE | 0.3 | 0.3 | 0.3 |
|  | BHT | 0.2 | 0.2 | 0.2 |
|  | MEHQ | 0.1 | 0.1 | 0.1 |
|  | PBZ | 3 | 3 | 3 |
|  | tBPB | 4 | — | 4 |
|  | p-TSS | 5 | 5 | 5 |
|  | GM27884 | 185 | 185 | 185 |
|  |  | Adhesion to tooth | Adhesion to tooth | |
| Bovine tooth enamel | | 15.4 MPa | 14.8 MPa | 12.0 MPa |
| SD | | 4.1 | 0.9 | 0.8 |

From the above, it was shown that the polymerization initiator systems containing PBZ shown in Tables 4 and 5 can be used as chemical polymerization initiator systems, and the curable composition containing the polymerization initiator system also has sufficient adhesion to tooth.

When the value of adhesive strength to tooth is 10 MPa or more, it can be determined that the curable composition containing the polymerization initiator of the present invention has sufficient adhesive strength.

The invention claimed is:

1. A kit for preparing a curable composition, comprising a first pack containing a compound (A) selected from the group consisting of a pyrazolidinedione compound and/or pyrazolidine (di) thione compound (A1), and a salt (A2) of the compound (A1), and
a second pack containing a transition metal compound (B),
wherein at least one of the first pack and the second pack contains a polymerizable monomer (C) and a peroxide (D).

2. The kit for preparing a curable composition according to claim 1,
wherein the pyrazolidinedione compound and/or pyrazolidine (di) thione compound (A1) is represented by the following general formula (1),

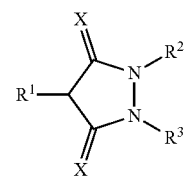

(1)

wherein $R^1$ is a hydrogen atom or a hydrocarbon group having 1 to 20 carbon atoms which may have a substituent, and the hydrocarbon group may contain a hetero atom,
$R^2$ and $R^3$ are independently a hydrogen atom or a hydrocarbon group having 1 to 12 carbon atoms which may have a substituent, and the hydrocarbon group may contain a hetero atom,
X represents an oxygen atom or a sulfur atom, and $R^2$ and $R^3$ may be directly bonded to each other to form a cyclic hydrocarbon group having 3 to 12 carbon atoms.

3. The kit for preparing a curable composition according to claim 1, wherein the transition metal compound (B) is a copper compound.

4. The kit for preparing a curable composition according to claim 1, wherein at least one of the first pack and the second pack contains at least one selected from the group consisting of a peroxide (D), a filler (E), a reducing agent (F), and an aqueous solvent (G).

5. The kit for preparing a curable composition according to claim 1, wherein at least one of the first pack and the second pack contains a photopolymerization initiator (H).

* * * * *